US011344669B2

(12) United States Patent
Agard et al.

(10) Patent No.: US 11,344,669 B2
(45) Date of Patent: May 31, 2022

(54) ROTARY PLUNGER PUMP SUBSYSTEMS

(71) Applicant: Eli Lilly and Company, Indianapolis, IN (US)

(72) Inventors: Ryan Michael Agard, Royersford, PA (US); Matthew James Clemente, Carmel, IN (US); Shaun Robert Devitt, Wayne, PA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 17/259,640

(22) PCT Filed: Aug. 21, 2020

(86) PCT No.: PCT/US2020/047331
§ 371 (c)(1),
(2) Date: Jan. 12, 2021

(87) PCT Pub. No.: WO2021/041184
PCT Pub. Date: Mar. 4, 2021

(65) Prior Publication Data
US 2021/0353853 A1    Nov. 18, 2021

Related U.S. Application Data

(60) Provisional application No. 62/895,140, filed on Sep. 3, 2019, provisional application No. 62/891,600, filed on Aug. 26, 2019.

(51) Int. Cl.
*A61M 5/142* (2006.01)
*F04B 7/06* (2006.01)

(52) U.S. Cl.
CPC ............ *A61M 5/14216* (2013.01); *F04B 7/06* (2013.01); *A61M 2205/103* (2013.01); *A61M 2205/106* (2013.01); *F04B 2201/02011* (2013.01)

(58) Field of Classification Search
CPC .. F04B 7/06; F04B 13/00; F04B 53/14; F04B 7/04; F04B 9/02; F04B 19/22;
(Continued)

(56) References Cited

U.S. PATENT DOCUMENTS 3,168,872 A * 2/1965 Pinkerton ................. F04B 7/06
417/492
4,008,003 A * 2/1977 Pinkerton ................. F04B 5/02
417/250

(Continued)

FOREIGN PATENT DOCUMENTS

DE    392328    3/1924
DE    3630528   9/1986

(Continued)

OTHER PUBLICATIONS

Patent Cooperation Treaty International Search Report pertaining to International Application No. PCT/US2020/047331; dated Nov. 11, 2020.

(Continued)

*Primary Examiner* — Scott J Medway
(74) *Attorney, Agent, or Firm* — Arthur C. H. Shum

(57) ABSTRACT

A rotary sub-assembly for pumping of fluid is provided. The sub-assembly includes a hollow body defining a cavity having a longitudinal axis, the body comprising a cavity wall with at least two ports passing therethrough. At least a portion of the cavity has a non-circular cross-section such that a first constant or varying radial distance from the longitudinal axis to inwardly-offset segments of the cavity wall surrounding the two ports is less than a second constant or varying radial distance from the longitudinal axis to second segments of the cavity wall spaced apart from the two ports. A rotatable plunger is housed in the cavity. The plunger is sized and shaped such that a side wall of the plunger can establish a liquid-tight seal against the inwardly- (Continued)

offset segments of the cavity wall, but does not establish a liquid-tight seal with the second segments of the cavity wall spaced apart from the two ports.

11 Claims, 18 Drawing Sheets

(58) Field of Classification Search
CPC ... F04B 1/124; F04B 53/148; A61M 16/0057; A61M 5/14216; A61M 5/1452
See application file for complete search history.

(56) References Cited

U.S. PATENT DOCUMENTS

| | | | |
|---|---|---|---|
| 4,968,230 A | 11/1990 | Progl | |
| 5,044,889 A * | 9/1991 | Pinkerton | F04B 49/005 |
| | | | 417/53 |
| 5,312,233 A * | 5/1994 | Tanny | F04B 7/0038 |
| | | | 417/316 |
| 5,472,320 A * | 12/1995 | Weisbrodt | F04B 7/06 |
| | | | 417/326 |
| 5,494,420 A * | 2/1996 | Mawhirt | F04B 7/06 |
| | | | 417/499 |
| 5,961,303 A * | 10/1999 | King | F04B 7/06 |
| | | | 417/492 |
| 7,785,084 B1 * | 8/2010 | Rawlings | F04B 23/06 |
| | | | 417/500 |
| 9,222,470 B2 * | 12/2015 | Genoud | A61M 5/14216 |
| 9,261,085 B2 * | 2/2016 | Middleton | F04B 53/166 |
| 9,726,172 B2 | 8/2017 | Wattellier et al. | |
| 10,393,096 B2 * | 8/2019 | Beard | F04B 7/0007 |
| 11,143,172 B2 * | 10/2021 | Rawlings | F04B 9/02 |
| 2013/0287608 A1 * | 10/2013 | Elliott | F04B 43/02 |
| | | | 417/435 |
| 2016/0121043 A1 | 5/2016 | Weibel | |
| 2018/0187663 A1 * | 7/2018 | Matson | F04B 53/20 |
| 2018/0266406 A1 * | 9/2018 | Bredbeck | F04B 53/14 |
| 2020/0217186 A1 * | 7/2020 | Mollatt | F04B 53/10 |

FOREIGN PATENT DOCUMENTS

| | | |
|---|---|---|
| WO | 9320864 | 10/1993 |
| WO | 12171572 | 12/2012 |

OTHER PUBLICATIONS

Patent Cooperation Treaty Written Opinion of the International Searching Authority pertaining to International Application No. PCT/US2020/047331; dated Nov. 11, 2020.

* cited by examiner

ROTARY PLUNGER PUMP SUBSYSTEMS

FIELD OF THE DISCLOSURE

The present disclosure relates to rotary plunger pump subsystems. More particularly, the present disclosure relates to rotary plunger pump systems for drug-delivery systems or devices.

BACKGROUND OF THE DISCLOSURE

Many drug-delivery systems are required to deliver a precise and accurate amount of drug fluid to a patient from a drug container or reservoir. The amount of drug fluid delivered may be less than the full amount of drug stored in the drug container or reservoir. Examples of such drug-delivery systems include, without limitation, insulin pens and pumps, devices configured to deliver multiple fixed-doses of a drug, and single-use drug-delivery devices requiring a patient-specific dose setting at time of administration.

SUMMARY

The present disclosure relates to rotary plunger pump subsystems. More particularly, the present disclosure relates to rotary plunger pump systems for drug-delivery devices.

Various aspects are described in this disclosure, which include, but are not limited to, the following aspects:

1. A rotary sub-assembly for pumping of drug fluid in a drug-delivery device, said sub-assembly comprising: a hollow body comprising a housing side wall defining a cavity extending about a longitudinal axis between a closed distal end and an open proximal end, the housing side wall including at least two ports passing therethrough and in fluid communication with the cavity, wherein at least a working portion of the cavity has a non-circular cross-section extending along a plane perpendicular to the longitudinal axis, the working portion being defined by first inwardly-offset segments of the housing side wall interconnected by second segments of the housing side wall, the first inwardly-offset segments spaced from the longitudinal axis by a constant or varying first radial distance, and the second segments spaced from the longitudinal axis by a constant or varying second radial distance that is greater than the first radial distance, wherein said first inwardly-offset segments of the housing side wall are disposed along regions of the side wall surrounding the two ports, and said second segments of the housing side wall are spaced apart from the two ports; and a plunger housed in the cavity defining a working chamber between the plunger and the housing side wall, wherein: the plunger is configured to rotate relative to the body in order to put the working chamber into sequential fluid-flow communication with at least one port of the two ports, then no port, then at least the other of said two ports, the plunger is further configured to move in longitudinal translation relative to the body and thereby cause a volume of said working chamber to vary in order to successively take in a drug fluid from one of the two ports and then to discharge the fluid from the other of the two ports, and the plunger is sized and shaped such that when the working chamber is in fluid-flow communication with one of the two ports, a side wall of the plunger establishes a liquid-tight seal against the first inwardly-offset segment of the housing side wall surrounding the other port of the two ports, but does not establish a liquid-tight seal with the second segments of the housing side wall.

2. The rotary sub-assembly of aspect 1, wherein the plunger further comprises a plunger pin extending radially outward from the plunger.

3. The rotary sub-assembly of aspect 2, wherein the body further comprises a first pumping track configured to slidably contact a distal side of the plunger pin as the plunger rotates relative to the body, wherein the pumping track comprises at least one flat section extending along a plane that is perpendicular to the longitudinal axis.

4. The rotary sub-assembly of aspect 3, wherein the pumping track comprises both a distal flat section extending along a plane that is perpendicular to the longitudinal axis and a proximal flat section extending along a different plane that is perpendicular to the longitudinal axis.

5. The rotary sub-assembly of aspect 2, wherein the body further comprises a first pumping track configured to slidably contact a distal side of the plunger pin, and a second pumping track configured to slidably contact a proximal side of the plunger pin.

6. The rotary sub-assembly of aspect 5, wherein the first pumping track and the second pumping track each comprise at least one flat section extending along a plane that is perpendicular to the longitudinal axis.

7. The rotary sub-assembly of any of aspects 1-6, wherein: a portion of the cavity has a circular cross-section along a plane perpendicular to the longitudinal axis, the plunger further comprises a proximal annular sealing rib and a distal annular sealing rib longitudinally spaced from one another, wherein both annular sealing ribs contact the portion of the cavity wall having the circular cross-section so as to establish a liquid-tight seal that seals the working chamber from the open proximal end of the cavity.

8. The rotary sub-assembly of aspect 7, wherein: the plunger is configured to move in longitudinal translation relative to the body between a proximal plunger position and a distal plunger position; and both annular sealing ribs on the plunger are located proximal to the two ports opening out into the cavity when the plunger is in its distal plunger position.

9. The rotary sub-assembly of aspect 8, wherein a longitudinal distance between the two annular sealing ribs is no less than a longitudinal distance between the proximal plunger position and the distal plunger position.

10. The rotary sub-assembly of any of aspects 1-9, wherein each of the first inwardly-offset segments of the housing side wall comprises a first edge that transitions smoothly to a first neighboring edge of said second segments of the housing side wall, and a second edge that transitions abruptly to a second neighboring edge of said second segments of the housing side wall.

BRIEF DESCRIPTION OF THE DRAWINGS

The above-mentioned and other features and advantages of this disclosure, and the manner of attaining them, will become more apparent and will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

In some embodiments, drug-delivery systems should ideally be small, so as to make them more easily portable and/or non-intrusive to the user. Such systems should also ideally comprise a relatively small number of simple components to make them more reliable and easier and less costly to manufacture. The system should also ideally be robust to minor imperfections in the shape and/or dimensions of the components (i.e., the required precision of the components should be relatively low) to make the system easier to manufacture. Finally, such systems should require only a small amount of energy to operate, so as to require less motive force from a user to use, or to decrease the need for bulky and/or expensive motors and batteries. There is therefore a need for pump subsystems that can deliver precise and accurate doses of drug fluids at high efficiency using a relatively small number of simple components, to achieve greater reliability and manufacturability.

Figure 1:
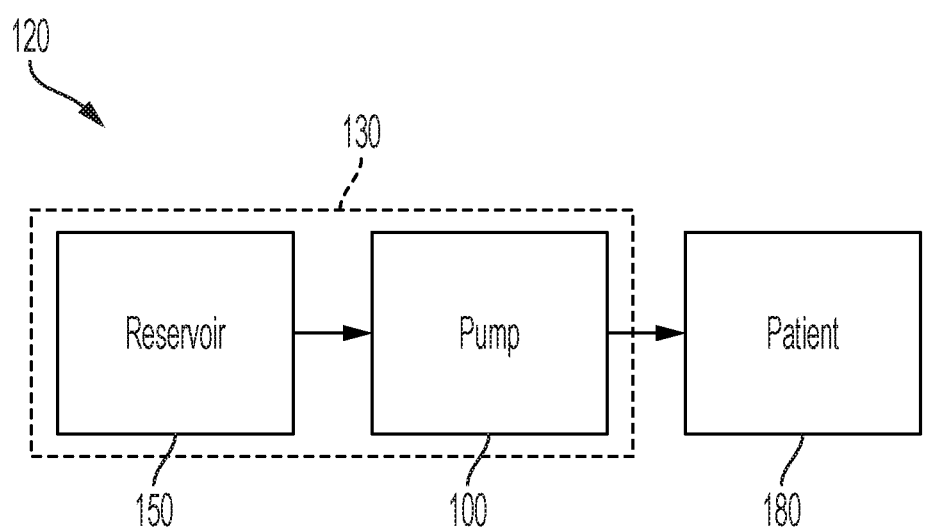
FIG. 1 depicts a drug delivery system comprising a rotary plunger pump subsystem, according to some embodiments.

FIG. 1 depicts a drug delivery system context 120, according to some embodiments. Context 120 includes a drug reservoir 150 storing a drug in a fluid form, a pump 100 that draws said drug fluid from reservoir 150, and delivers it to a patient 180, either through subcutaneous/intramuscular injection, or through other means. The reservoir 150 may store drug fluid under pressure, or may not store drug fluid under pressure (i.e., store drug fluid at ambient pressure). In some embodiments, drug reservoir 150 and pump 100 may be integrated into a single drug-delivery device system 130. In other embodiments, drug reservoir 150 and pump 100 may comprise or be integrated into separate devices. Pump 100 may be a rotary plunger pump subsystem, such as the subsystems disclosed herein; such a pump subsystem may be either manually or electronically controlled.

The term "drug" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the above device. The drug as used in the device may be formulated with one or more excipients. Such a drug-delivery device may be operated in a manner generally described herein by a patient, caregiver, or healthcare professional to deliver one or more drugs to a person.

Using a rotary plunger pump to deliver drug fluid poses several challenges. For example, previously-known rotary plunger pumps generally use rigid components. While these rigid components may provide adequate sealing for industrial applications, rigid-on-rigid sealing interfaces for dynamic seals is not generally adequate for maintaining the sterility and integrity of a drug reservoir and drug fluid path in a drug-delivery device. Also, using rigid components for dynamic seals require high-precision parts that are not cost-effective for disposable medical devices.

At least some embodiments of the pump subsystem described herein therefore use elastomeric surfaces to create fluid-tight seals. For example, at least a portion of the rotating plunger may comprise an elastomeric sleeve that interfaces with the rigid interior wall of the pump housing to create a dynamic, fluid-tight seal. However, use of such elastomeric surfaces can decrease the efficiency and/or accuracy of the pump subsystem. As described in further detail herein, the disclosed pump subsystems utilize different features and/or configurations to increase the efficiency and accuracy of the pump subsystem.

Figure 2:
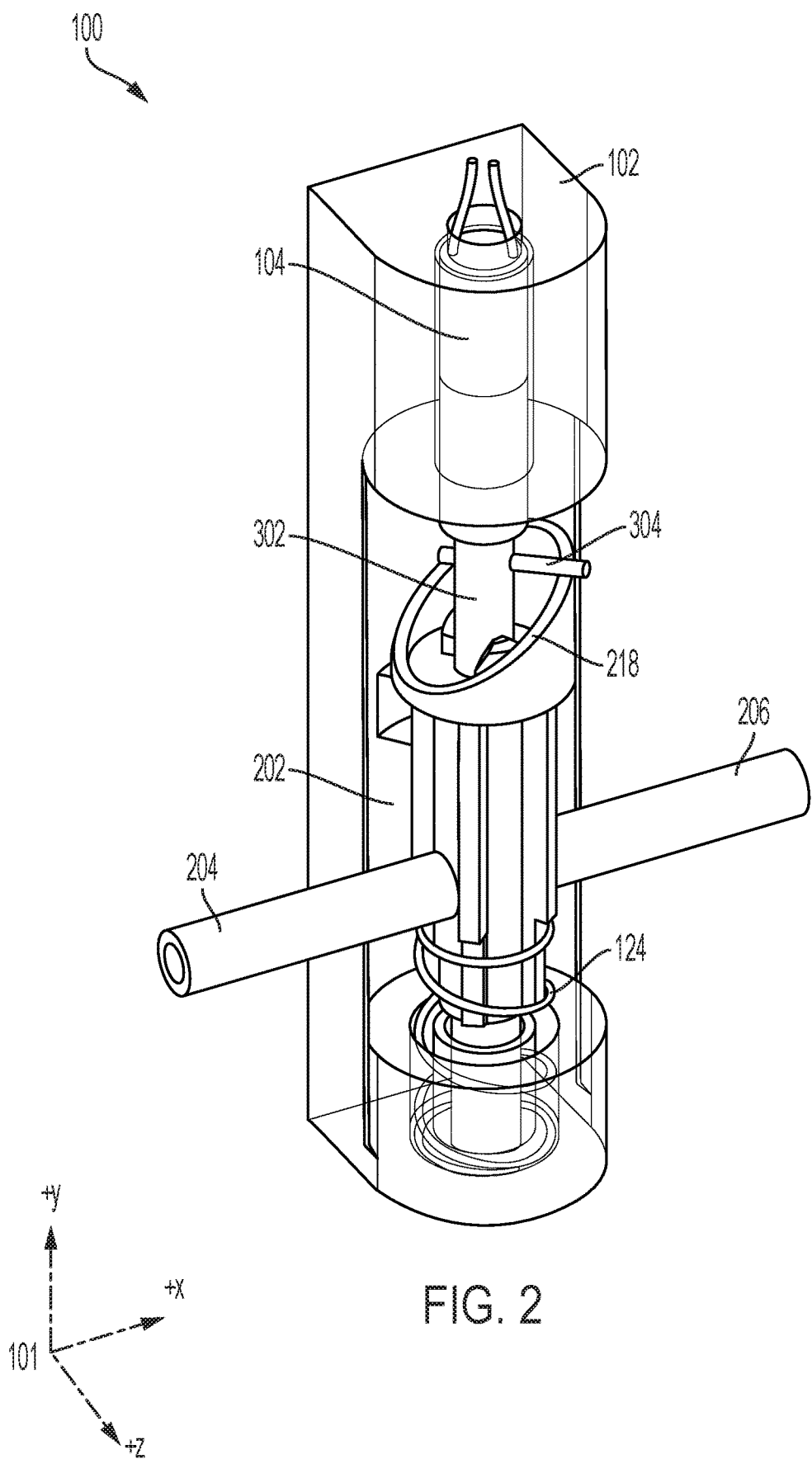
FIG. 2 depicts a rotary plunger pump subsystem, according to some embodiments.

Solely for ease of explication, FIG. 2 and all subsequent figures will use the x, y, z directional system depicted by arrows 101. In the specification and claims, references to the "proximal" or "upwards" direction shall mean the positive y direction; references to the "distal" or "downward" direction shall mean the negative y direction.

Figure 3:
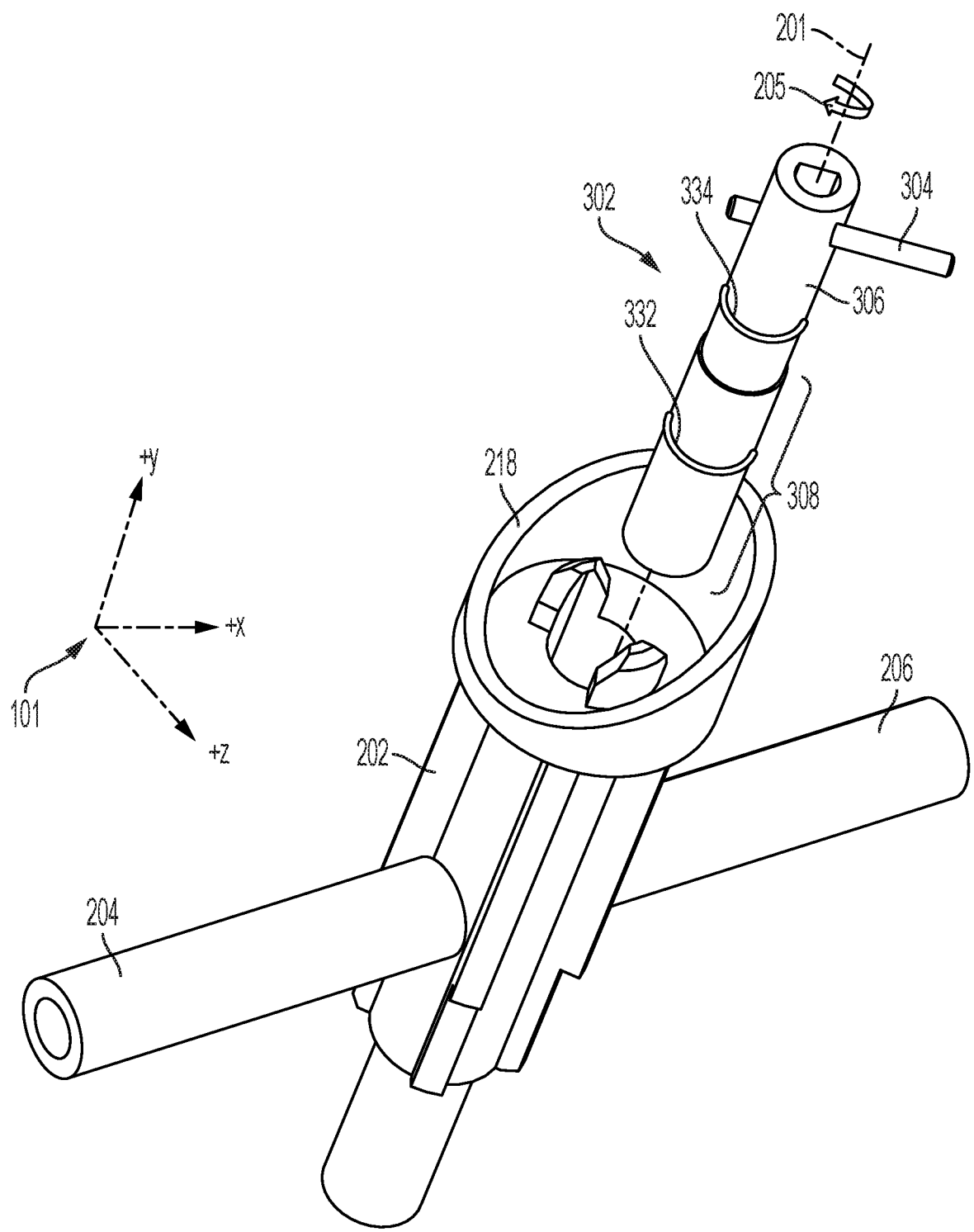
FIG. 3 depicts an exploded view of certain components of the rotary plunger pump system of FIG. 2, according to some embodiments.
Figure 4A:
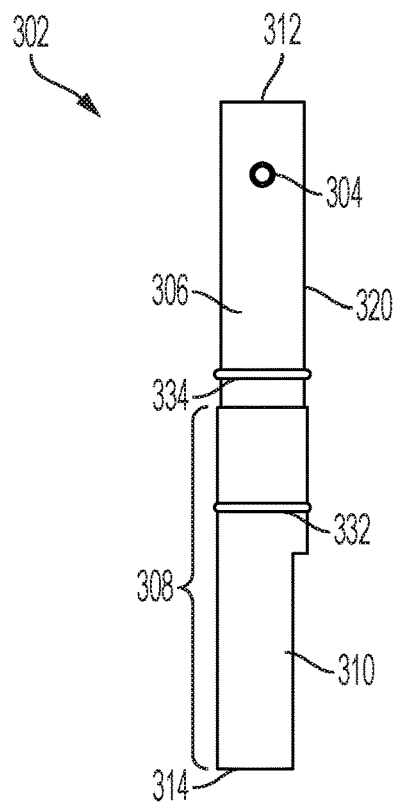
FIGS. 4A, 4B, 4C, and 4D provide profile views of a plunger component of the rotary plunger pump system, according to some embodiments.
Figure 4B:
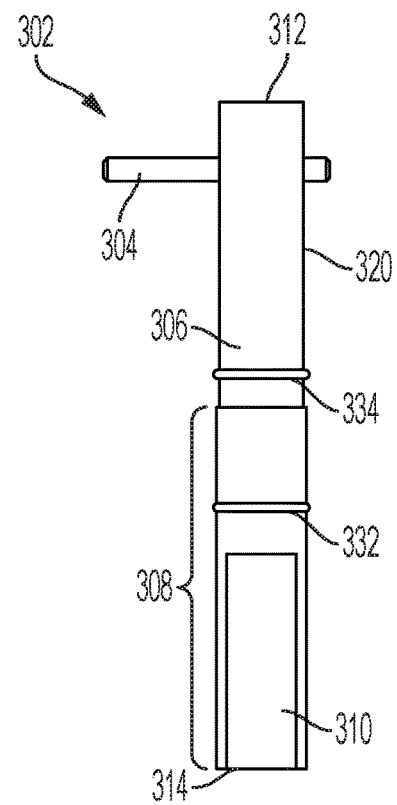
Figure 4C:
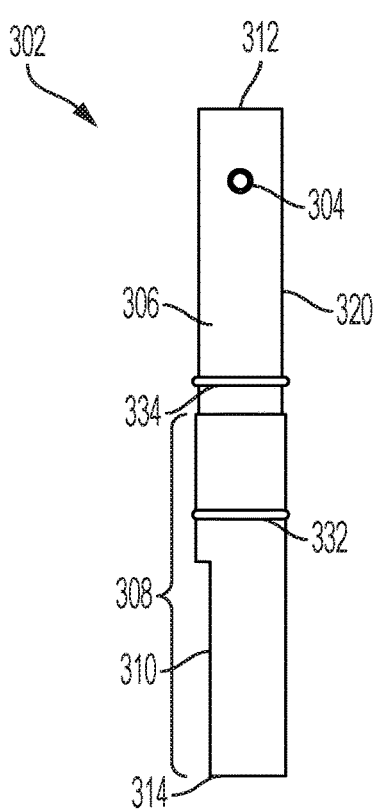
Figure 4D:
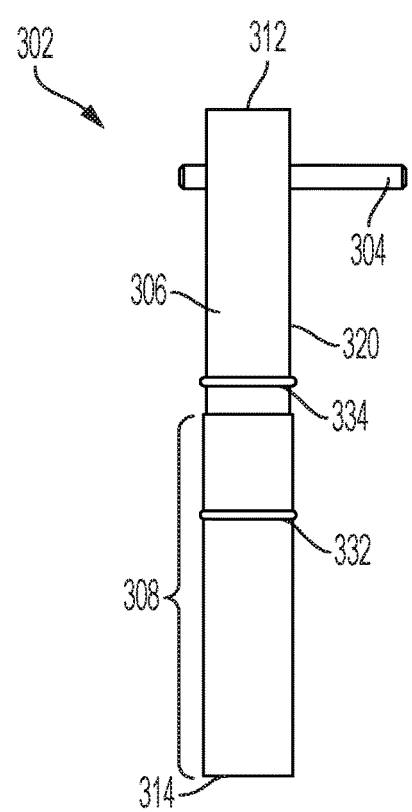

FIGS. 2 and 3 depict a rotary plunger pump subsystem 100, according to some embodiments. Rotary plunger pump subsystem 100 may be used to pump any suitable fluid. In some embodiments, subsystem 100 may be used as part of a drug-delivery device for pumping a drug fluid.

Subsystem 100 includes mounting frame 102, rotary drive shaft 104, rotating plunger 302, pump housing 202, and return spring 124. A proximal end of frame 102 supports a rotary drive shaft 104, which is in turn connected to rotating plunger 302. Rotary drive shaft 104 may be connected to a drive motor, a spring (e.g., a torsion spring, or a power/clock spring), a manual user-operated crank, knob, button, lever, or other actuator, or other source of torque to drive rotating plunger 302 to rotate about longitudinal axis 201 in the direction of arrow 205 (e.g., in a clockwise direction), as shown in FIG. 3.

Figure 5:
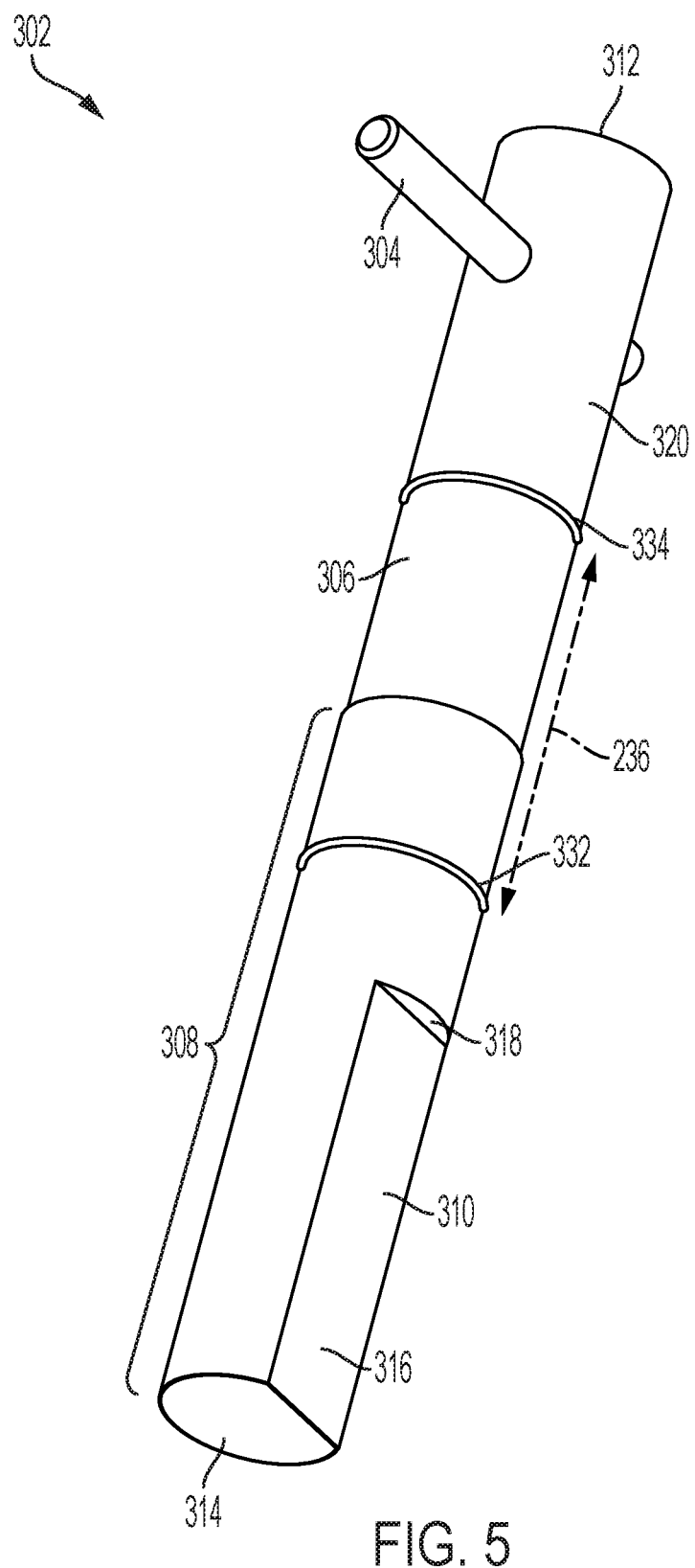
FIG. 5 provides a perspective view of the plunger component, according to some embodiments.

FIGS. 4A-4D and 5 depict the rotating plunger 302 in more detail, according to some embodiments. FIGS. 4A-4D depict plunger 302 from four separate profile views, while FIG. 5 provides a perspective view. Plunger 302 comprises a substantially cylindrical elongated body having a proximal end 312 and a distal end 314 connected by curved, cylindrical side wall 320. In some embodiments, the cylindrical body of plunger 302 may comprise a proximal rigid rod 306 (e.g., constructed at least partly from a suitable metal or rigid plastic) coupled to a relatively pliable/deformable distal sleeve 308. Since sleeve 308 is configured to come into contact with the drug fluid, sleeve 308 may be constructed from a drug-compatible flexible sealing material, such as, for example, an elastomer (such as bromobutyl, chlorobutyl, or a blend of either of the two with other rubbers such as polyisoprene or styrene-butadiene), an inert soft plastic (such as polytetrafluoroethylene, ethylene tetrafluoroethylene, polyethylene, or fluorinated ethylene propylene), or a rubber coated with a film or coating of an inert plastic. The rigid rod 306 may have a slit-shaped, cross-shaped, T-shaped, or other shape cross-section that inserts into a corresponding opening in sleeve 308 to prevent excessive twisting of sleeve 308 relative to rod 306 about longitudinal axis 201. Sleeve 308 may be coupled to rod 306 using a pressure fit, an interference fit, an adhesive, an ultrasonic or heat weld, or other suitable coupling methods. In other embodiments, the cylindrical body of plunger 302 may be constructed as a single monolithic piece. The cylindrical body of plunger 302 may further comprise at least two sealing elements, a distal annular sealing rib 332 and a proximal annular sealing rib 334, that surround a transverse circumference of plunger 302. In some embodiments, the two ribs may also comprise an elastomeric material suitable for creating a dynamic fluid-tight seal against a rigid surface. The two ribs 332, 334 may be spaced a longitudinal distance 236 apart. In some embodiments, a third "middle" rib (not shown) may also be provided between ribs 332, 334 to function as additional structural support and to provide an additional (potentially redundant) seal between working chamber 602 (described below with reference to FIGS. 9A-9B) and exterior atmosphere.

Plunger pin 304 protrudes radially outward from side wall 320 of plunger 302 and may be rigidly affixed thereto. In some embodiments, pin 304 and rod 306 may be formed of one monolithic piece; in other embodiments, pin 304 may be a separate part that is adhered, joined, inserted, or molded into rod 306. As depicted, pin 304 may be disposed adjacent to proximal end 312 of plunger 302. However, the pin may be disposed at any point along the length of plunger 302. As best seen in FIG. 5, plunger 302 may include a reduced cross-sectional area distal portion that may be defined by a cutout 310 disposed adjacent to the distal end 314. Cutout 310 is defined by a substantially planar longitudinal portion 316 recessed below the side wall 320 and connected to a lip 318 which steps inwards from the cylindrical side wall 320 of plunger 302. Portion 316 and lip 318 may intersect in a transverse relationship. In one embodiment, planar portion 316 of cutout 310 faces a first radial direction, and the pin 304 extends in a second radial direction that is perpendicular to the first radial direction of the placement of the cutout.

Figure 6:
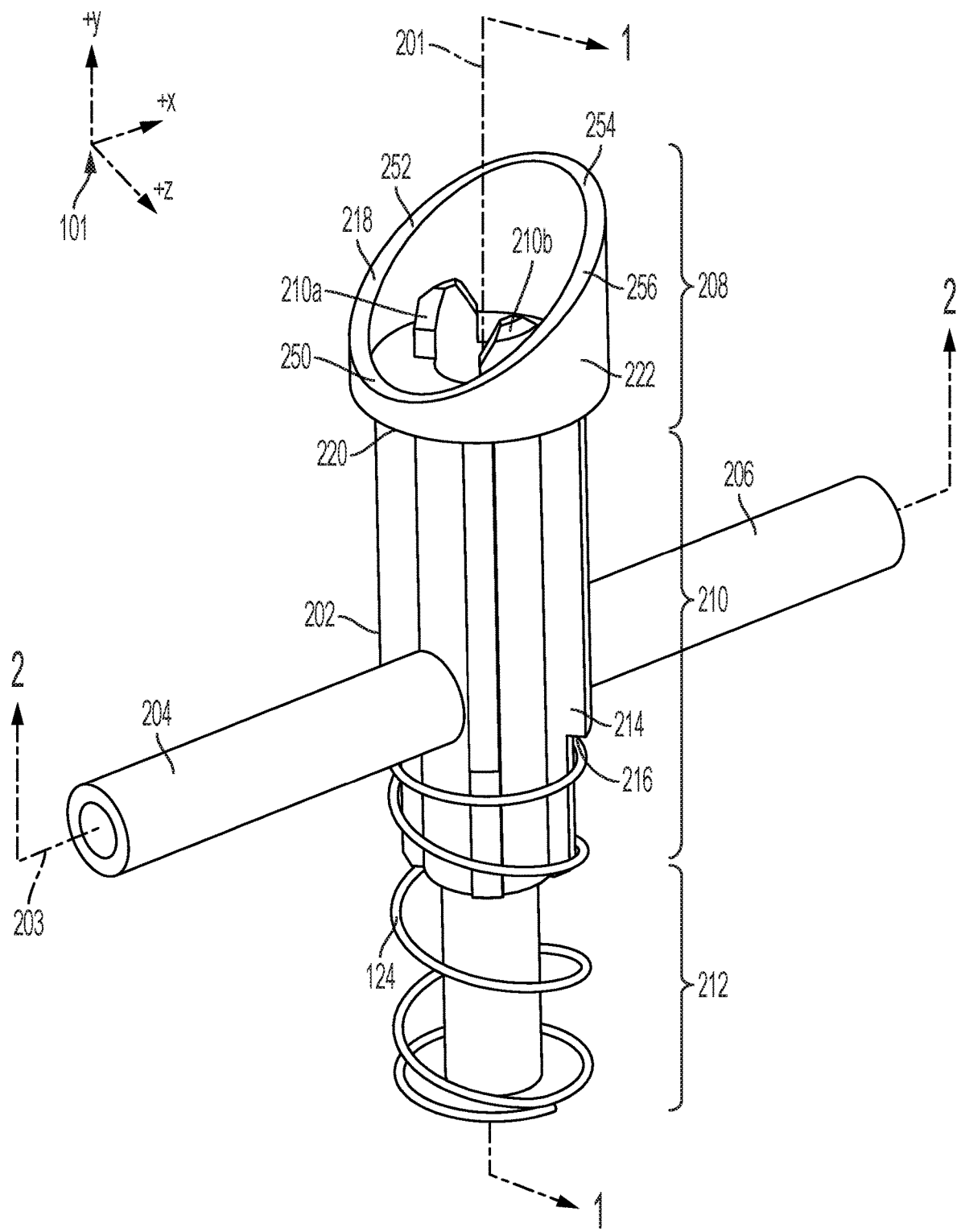
FIG. 6 provides a perspective view of a pump housing component of the pump subsystem, according to some embodiments.
Figure 7A:
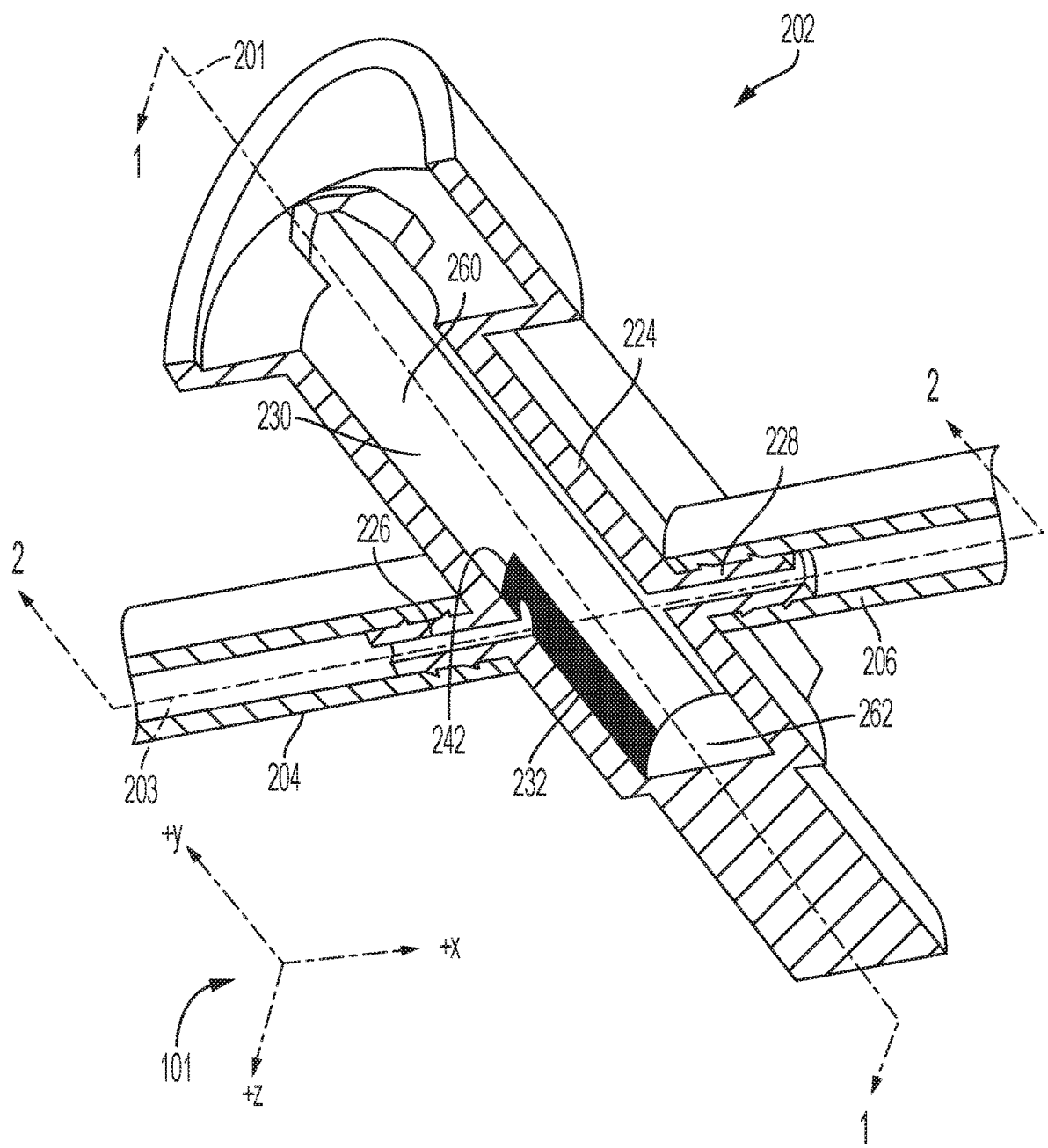
FIGS. 7A and 7B provide perspective, cross-sectional views of the pump housing component, according to some embodiments.
Figure 7B:
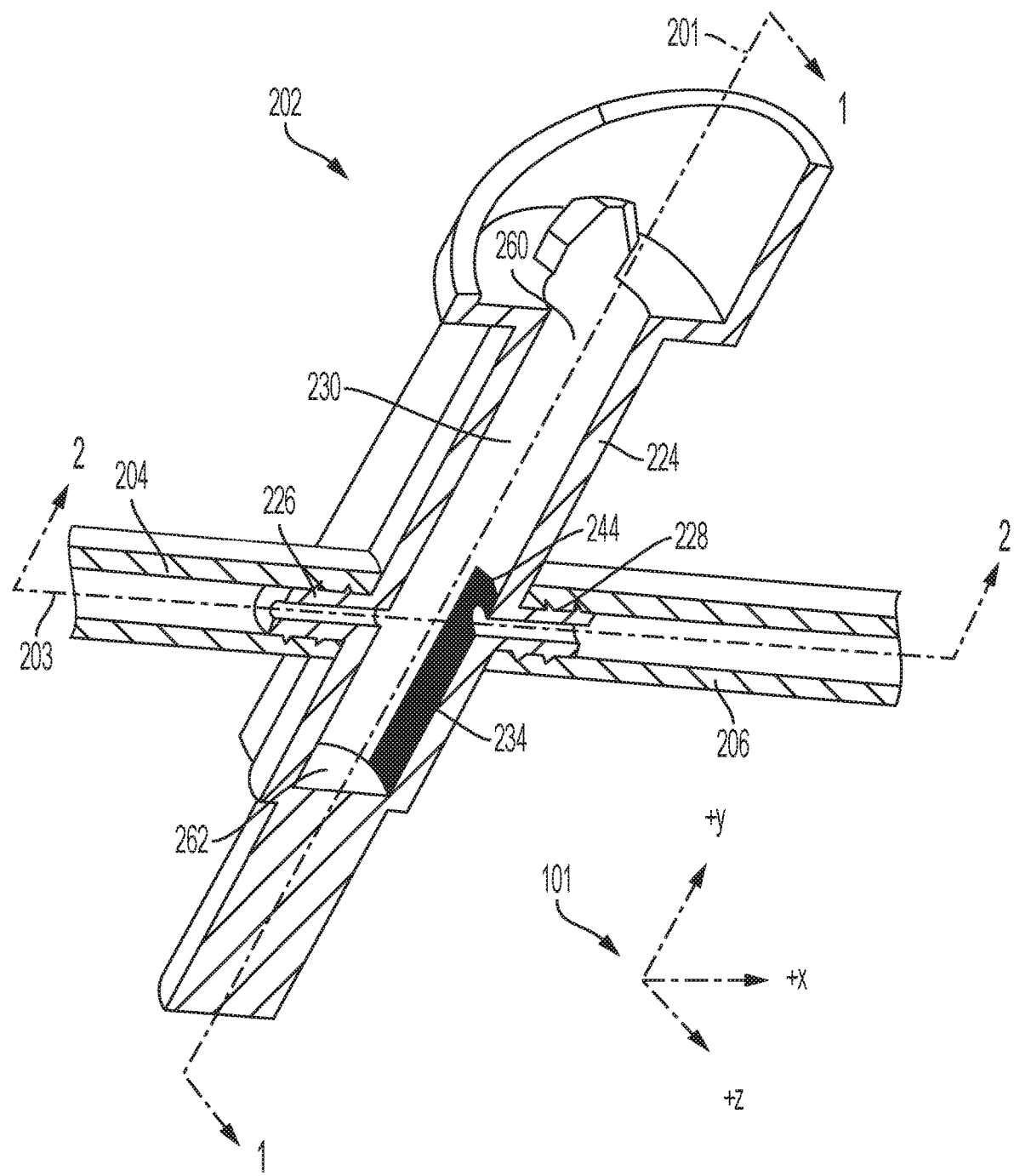
Figure 8:
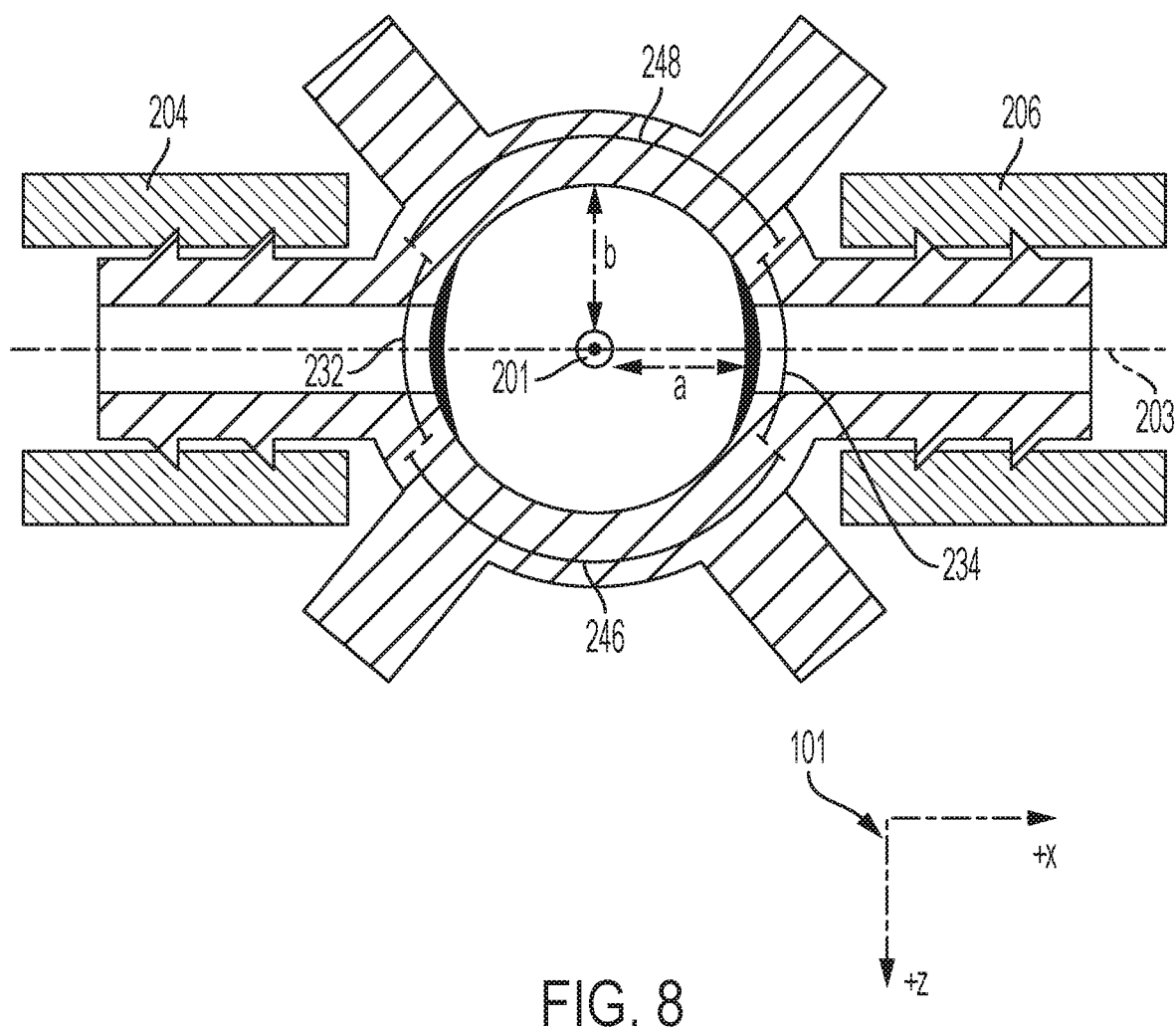
FIG. 8 provides a top-down, cross-sectional view of the pump housing, according to some embodiments.

Plunger 302 is received within pump housing 202. One exemplary embodiment of housing 202 is depicted in greater detail in FIGS. 6, 7A, 7B, and 8. FIG. 6 provides a perspective view of housing 202, FIGS. 7A and 7B provide a cross-sectional view of housing 202 along line 1-1, and FIG. 8 provides a cross-sectional, top-down view of housing 202 along line 2-2 (e.g., as viewed from the positive y direction). Housing 202 may be constructed from any suitable and relatively rigid material, such as an olefin plastic (e.g., cyclic olefin copolymer, cyclic olefin copolymer, and/or polypropylene). The interface between housing 202 and plunger 302 may be lubricated with an appropriate pharmaceutical container lubricant, such as silicone oil.

As best shown in FIG. 6, housing 202 comprises three sections: a proximal section 208, an intermediate section 210, and a distal section 212, each disposed along a common axis 201. Proximal section 208 comprises a side wall 222 that defines an angled pin track 218. Pin track 218 is angled such that a plane defined by track 218 is not perpendicular to longitudinal axis 218, but is angularly offset such that a proximal end 254 of track 218 is higher than (i.e., proximal to) the opposite, distal end 250 of track 218. Distal end 250 is connected to proximal end 254 of track 218 via an upwardly-sloping portion 252, and a downwardly-sloping portion 256. Proximal section 208 also comprises two tabs 210a, 210b that receive and support plunger 302.

Intermediate section 210 comprises a side wall 224, and one or more axial ridges 214 projecting radially outward from side wall 224. One or more of the ridges 214 have a radially inward step 216 oriented towards a distal end of housing 202. As best shown in FIGS. 7A and 7B, side wall 224 defines a cavity 230 internally along the axis 201 having an open proximal end 260 and a closed distal end 262. Side wall 224 also defines an inlet port 226 and an outlet port 228, shown defined by radially extending arms. In one embodiment, the ports 226, 228 are oriented in different radial directions. In one embodiment, the ports 226, 228 are oriented extending in opposite directions (for example, angularly spaced 180 degrees from each other) along a transverse axis 203 that extends orthogonal to the longitudinal axis 201. Inlet port 226 and outlet port 228 pass through side wall 224 and are in fluid communication with cavity 230. Ducts are shown disposed on the arms in a fluid tight seal. Inlet port 226 is fluidically connected with an inlet duct 204, while outlet port 228 is fluidically connected to an outlet duct 206. During operation of the pump subsystem, fluid is sucked in through inlet port 226/inlet duct 204 and into the cavity 230, and expelled through outlet port 228/outlet duct 206.

The interior surface of the side wall 224 that faces cavity 230 may also include two inward offsets 232 and 234 (shaded solid black in FIGS. 7A and 7B). Inward offsets are disposed on portions of side wall 224 adjacent to and/or surrounding the inlet port 226 and the outlet port 228, respectively. In some embodiments, inward offsets 232, 234 extend downwards (distally) all the way to the closed, distal end 262 of cavity 230 as depicted—this can improve the manufacturability of housing 202 using injection molding. In other embodiments, inward offsets 232, 234 do not extend distally all the way to closed distal end 262. Inward offsets 232, 234 also terminate a short distance above ports 226, 228 in the proximal direction at upward lip 242, 244 respectively. The section of cavity 230 above (i.e., proximal to) upward lips 242, 244 have a generally circular cross-section. However, as best shown in FIG. 8, the inward offsets 232 and 234 cause cavity 230 to have a non-circular cross-section along the transverse plane defined by transverse axis 203 and perpendicular to longitudinal axis 201. Specifically, housing side wall 224 that defines cavity 230 comprises first inwardly-offset segments 232, 234 interconnected by second segments 246, 248. The first inwardly-offset segments 232, 234 are spaced from longitudinal axis 201 by a constant or varying first radial distance "a." The second segments 246, 248 are spaced from longitudinal axis 201 by a constant or varying second radial distance "b" that is greater than the first radial distance "a". The first inwardly-offset segments 232, 234 are disposed along regions of the side wall 224 surrounding the two ports 226, 228, whereas the second segments 246, 248 of the side wall 224 are spaced apart from the two ports. Since inward offsets 232, 234 extend downward to the closed, distal end of cavity 230, cross-sections of cavity 230 perpendicular to longitudinal axis 201 and taken below (i.e., distal to) transverse axis 203 are similarly non-circular in shape.

Returning to FIG. 6, distal section 212 of housing 202 comprises a substantially cylindrical body having a smaller cross-sectional area compared to proximal section 208 and intermediate section 210. Distal section 212 may also take the form of other shapes. Return spring 124 may be wrapped around distal section 212 such that a proximal end of spring 124 abuts the inward step 216 of one or more of the ridges 214 (see FIG. 6), and a distal end of spring 124 abuts and/or is received within a receptacle on mounting frame 102 (see FIG. 2). Thus mounted, return spring 124 provides upward biasing pressure against housing 202.

When plunger 302 is received within housing 202, distal sleeve 308 of plunger 304 is received within cavity 230. The sleeve 308 and the cavity 230 are dimensioned such that the sleeve 308 fits tightly against inward offsets segments 232, 234, but only loosely and/or intermittently contacts (or does not contact at all) other portions (non-inward offset portions) of the interior wall of cavity 230 (e.g., second segments 246, 248). For example, the sleeve 308 and cavity 230 may be dimensioned such that the portions of the elastomeric surface of sleeve 308 in contact with inward offset segments 232, 234 experience relatively greater compression and/or deformation—in contrast, portions of the elastomeric surface of sleeve 308 in contact with other portions of the interior wall of cavity 230 (e.g., second segments 246, 248) may experience relatively less compression/deformation, or no compression/deformation. In some embodiments or cases, the sleeve 308 may not contact, or only intermittently contact, these other portions of the interior wall of cavity 230.

Plunger 302 is configured to rotate about longitudinal axis 201 within cavity 230. Plunger 302 is also configured to translate longitudinally along longitudinal axis 201 within cavity 230. The upward biasing pressure of return spring 124 causes the pin track 218 to abut and/or engage against the distal side (i.e., the underside) of plunger pin 304 at all times while plunger 302 rotates within cavity 230. When plunger 302 is received within cavity 230, the surfaces that define cutout 310 (that is, surfaces 316, 318) and the interior wall of cavity 230 (i.e., the interior surface of side wall 224) together define a working chamber 602 (see FIGS. 9A-9D) that is brought into repeated and sequential fluid-flow communication with no port, then the inlet port, then no port, and then the outlet port as the plunger moves within the cavity.

In operation, a motor, a stored energy device (e.g., a spring), and/or a user provides a rotary force to drive shaft 104. The rotary force causes shaft 104 and plunger 302 to rotate about longitudinal axis 201 in the direction of arrow 205 (see FIG. 3, FIGS. 9A-9D). As plunger 302 rotates within cavity 302, the plunger 302 and housing 202 successively move through the series of configurations depicted in FIGS. 9A-9D, and 10A-10D. Each of FIGS. 9A-9D show a profile, cross-sectional view of pump subsystem 100 along line 1-1, when viewed from the positive z direction. Each of FIGS. 10A-10D show a top-down, cross-sectional view of pump subsystem 100 along line 2-2, when viewed from the positive y direction. For clarity, the position of plunger pin 304 is outlined in phantom in FIGS. 10A-10D.

Figure 9A:
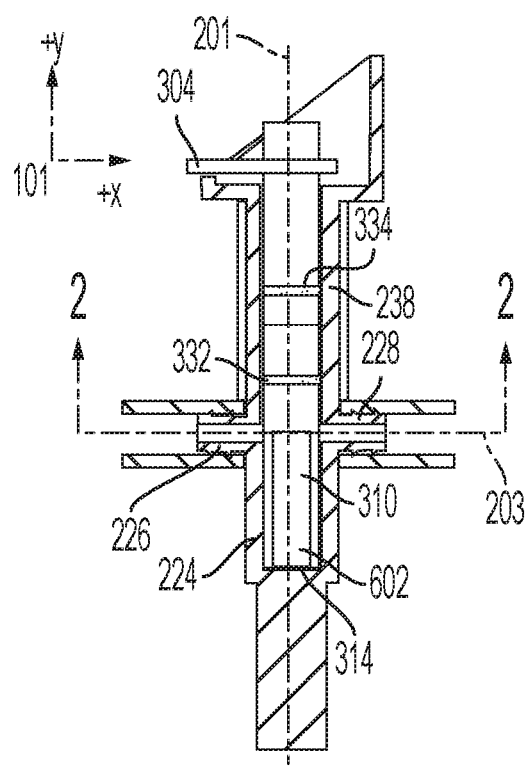
FIGS. 9A, 9B, 9C, and 9D provide profile, cross-sectional views of the pump subsystem in operation, according to some embodiments.
Figure 10A:
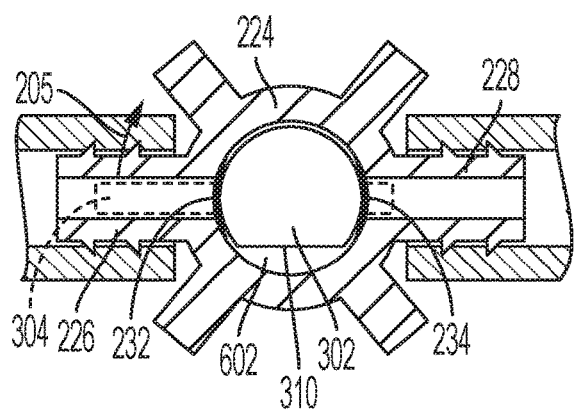
FIGS. 10A, 10B, 10C, and 10D provide top-down, cross-sectional views of the pump subsystem in operation, according to some embodiments.

In FIG. 9A and FIG. 10A, plunger 302 is rotated such that plunger pin 304 is pointed towards the negative x direction (i.e., to the left in FIG. 9A and FIG. 10A). When plunger pin 304 is pointed in this direction, spring 124 causes pin 304 to engage against the lowest portion (i.e., distal end 250) of pin track 218, thus causing plunger 302 to translate longitudinally to its furthest distal position within cavity 230 relative to housing 202. When plunger 302 is at this furthest distal position, both distal rib 332 and proximal rib 334 are located above (i.e., proximal to) the upward lips 242, 244 of internal offset segments 232, 234, where the cross-section of cavity 230 is circular in shape. Also while plunger 302 is at this furthest distal position, proximal rib 334 is located at starting position 238 along the interior wall of cavity 230. Distal rib 332 and proximal rib 334 are dimensioned and configured to press tightly against the interior wall of cavity 230 above internal offsets 232, 234 so as to establish a fluid-tight seal between working chamber 602 and external atmosphere. In this way, ribs 332, 334 preserve the sterility of working chamber 602 and the fluids passing therethrough.

Furthermore, while plunger 302 is at this furthest distal position, distal end 314 of plunger 302 may come into contact with the closed distal end 262 of cavity 230 (or be located close to the distal end of cavity 230), such that working chamber 602 has the smallest volume of any of the four configurations depicted in FIGS. 9A-9D and 10A-10D. In some embodiments, the volume of working chamber 602 while plunger 302 is at this furthest distal position should be configured to be relatively small, so as to reduce waste of drug fluid. Also, cutout 310 is oriented towards the positive z direction (i.e., out of the page in FIG. 9A, and downwards in FIG. 10A). As previously mentioned, cutout 310 and the interior wall of cavity 230 (i.e., the interior surface of side wall 224) define a working chamber 602. When cutout 310 is oriented towards the positive z direction, the curved side wall 320 of plunger 302 presses tightly against the inwardly offset segments 232, 234 surrounding inlet port 226 and outlet port 228, respectively, so as to establish a fluid-tight seal that blocks both ports. As a result, working chamber 602 is not in fluid communication with either port while in this configuration. However, as previously described, curved side wall 320 of plunger 302 may only loosely contact, or not contact at all, other portions of the interior wall of cavity 230 spaced apart from the two ports, such as second segments 246, 248 indicated in FIG. 8. The minimal contact, or no contact, reduces rotational friction between plunger 302 and housing 202, thus decreasing the amount of rotational force required to turn plunger 302.

Figure 9B:
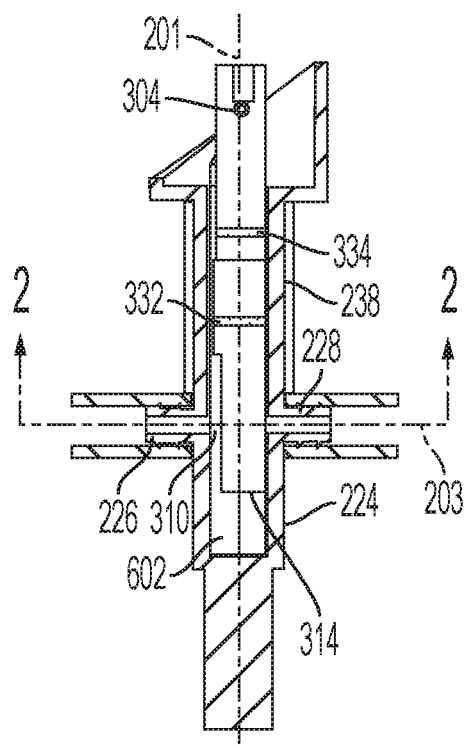
Figure 10B:
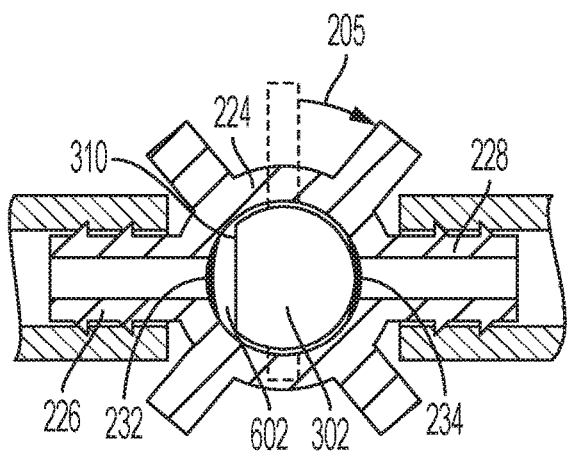

In FIG. 9B and FIG. 10B, plunger 302 is rotated such that plunger pin 304 is pointed towards the negative z direction (i.e., into the page in FIG. 9B, and upwards in FIG. 10B). When plunger pin 304 is pointed in this direction, spring 124 causes pin 304 to engage against upwardly-sloping portion 252 of pin track 218. This causes plunger 302 to translate longitudinally in the proximal direction relative to housing 202 as plunger 302 rotates, thus increasing the volume of working chamber 602. Also in this configuration, cutout 310 is oriented towards the negative x direction (i.e., to the left in FIG. 9B and FIG. 10B), thus opening fluid communication between working chamber 602 and inlet port 226. The opened fluid communication and the increasing volume of working chamber 602 causes fluid to be sucked into working chamber 602 from inlet port 226 as pin 304 rotates (or, if the fluid is stored under pressure in the drug reservoir, allows fluid to enter working chamber 602). In this configuration, curved side wall 320 of plunger 302 continues to press tightly against inwardly offset segment 234, thus maintaining the fluid-tight seal that blocks outlet port 228. As previously mentioned, curved side wall 320 only loosely contacts, or does not contact at all, other portions of the interior wall of cavity 230 spaced apart from the two ports, such as second segments 246, 248 indicated in FIG. 8.

Figure 9C:
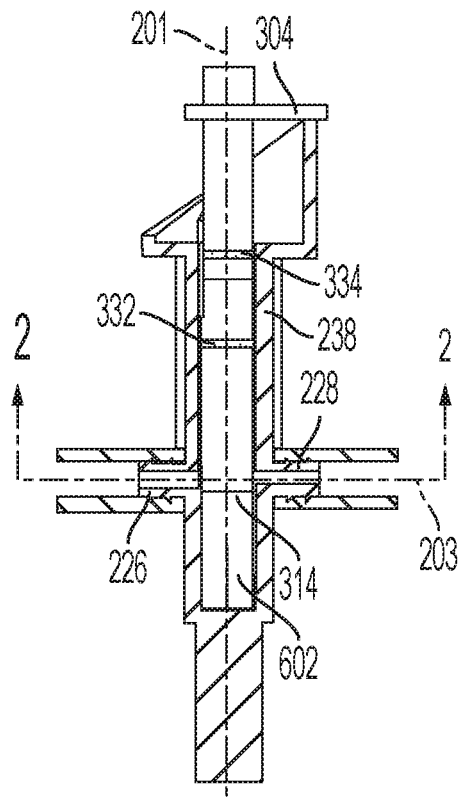
Figure 9D:
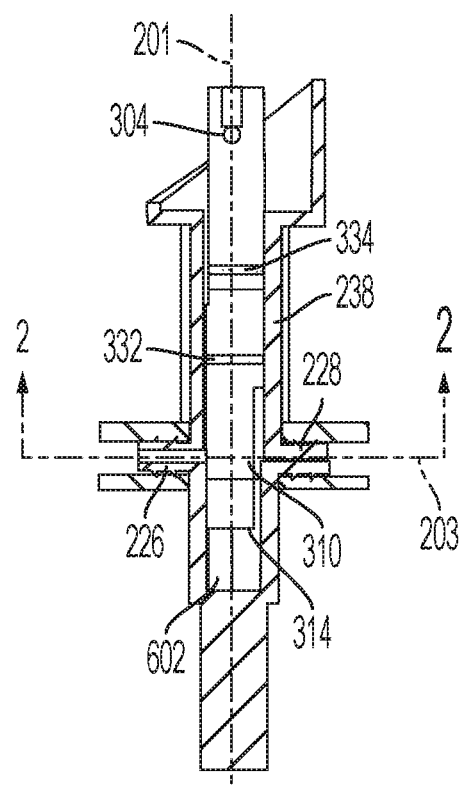
Figure 10C:
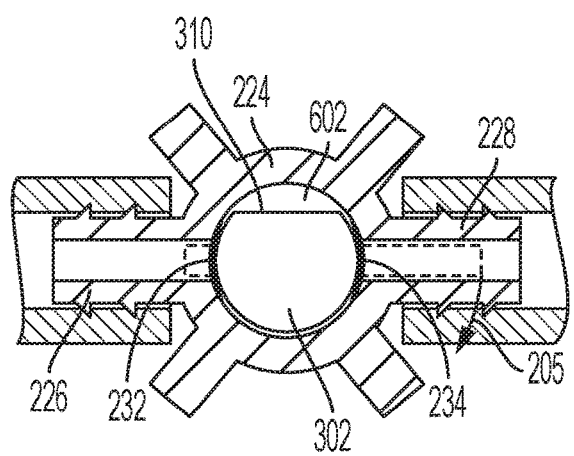

In FIG. 9C and FIG. 10C, plunger 302 is rotated such that plunger pin 304 is pointed towards the positive x direction (i.e., to the right in FIG. 9C and FIG. 10C). When plunger pin 304 is pointed in this direction, spring 124 causes pin 304 to engage against the highest portion (i.e., proximal portion 254) of pin track 218, thus allowing plunger 302 to translate longitudinally to its furthest proximal position within cavity 230 relative to housing 202. When in this configuration, distal end 314 of plunger 302 is located at its furthest proximal position within cavity 230 such that working chamber 602 is at its largest volume of any of the four configurations depicted in FIGS. 9A-9D and 10A-10D. Furthermore, ribs 332, 334 continue to provide a fluid-tight seal between working chamber 602 and external atmosphere so as to preserve the sterility of working chamber 602 and the fluids flowing therethrough. In some embodiments, distal rib 332 is located on plunger 302 such that, when plunger 302 occupies its furthest proximal position, distal rib 332 remains at or below (i.e., distal to) starting position 238. Said another way, ribs 332, 334 may be disposed on plunger 302 such that the longitudinal distance 236 between the two ribs is equal to or greater than the pump stroke, i.e., the difference in longitudinal position of plunger 302 as it translates between its furthest distal position and its furthest proximal position. This helps ensure that distal rib 332 remains distal to starting position 238 even while plunger 302 is located at its furthest proximal position. This helps ensure that no non-sterile area passes through both ribs, thus maintaining sterility inside working chamber 602 before, during, and after each pump cycle.

Also, while plunger 302 is at its furthest proximal position, cutout 310 is oriented towards the negative z direction (i.e., into the page in FIG. 9C, or upwards in FIG. 10C). When cutout 302 is so oriented, the curved side wall 320 of plunger 302 again establishes a fluid-tight seal against both inlet port 226 and outlet port 228, which means the working chamber 602 is not in fluid communication with either port. Once again, curved side wall 320 only loosely contacts, or does not contact at all, other portions of the interior wall of cavity 230 spaced apart from the two ports, such as second segments 246, 248 indicated in FIG. 8.

Figure 10D:
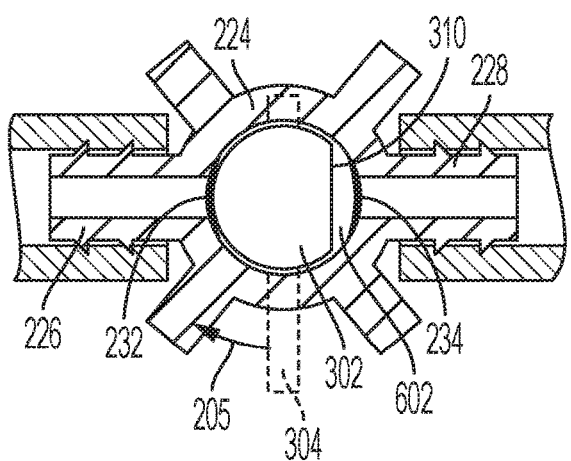

In FIG. 9D and FIG. 10D, plunger 302 is rotated such that plunger pin 304 is pointed towards the positive z direction (i.e., out of the page in FIG. 9D, or downwards in FIG. 10D). When plunger pin 304 is pointed in this direction, spring 124 causes pin 304 to engage against the downwardly-sloping portion 256 of pin track 218. This causes plunger 302 to translate longitudinally in the distal direction relative to housing 202 as plunger 302 rotates, thus decreasing the volume of working chamber 602. Also in this configuration, cutout 310 is oriented towards the positive x direction (i.e., to the right in FIGS. 9D and 10D), thus opening fluid communication between working chamber 602 and outlet port 228. The opened fluid communication and the decreasing volume of working chamber 602 causes fluid to be expelled from working chamber 602 and out through outlet port 228 as pin 304 rotates. In this configuration, curved side wall 320 of plunger 302 continues to press tightly against inwardly offset segment 232, thus maintaining the fluid-tight seal that blocks inlet port 226. As previously mentioned, curved side wall 320 only loosely contacts, or does not contact at all, other portions of the interior wall of cavity 230 spaced apart from the two ports, such as second segments 246, 248 indicated in FIG. 8.

A complete pump cycle comprises the four configurations described above in FIGS. 9A-9D and 10A-10D. During the pump cycle, sidewall 320 of plunger 302 only presses tightly against the interior wall of cavity 230 at a few critical points as plunger 302 rotates relative to housing 202. Specifically, plunger 302 presses tightly against inwardly offset segments 232, 234, and ribs 332, 334 presses tightly against the interior wall of cavity 230. These points of contact provide the fluid-tight seals necessary to draw in and expel fluid, as well as to isolate working chamber 602 from external atmosphere and contaminants. While other portions of plunger 302 may loosely or intermittently come into contact with other portions of interior housing, plunger 302 and/or housing 202 may be configured to minimize or avoid entirely such additional, extraneous contacts in order to reduce rotational friction between plunger 302 and housing 202, thereby increasing the efficiency of the pump subsystem.

Inwardly offset segments 232, 234 may take the form of different shapes. For example, FIGS. 11A-D depict several illustrative offsets, each of which have different shapes. Each of FIGS. 11A-D depict a simplified, top-down, cross-sectional view of housing 202 taken along line 2-2, when viewed from the positive y direction. For the sake of illustration, these figures have not been drawn to scale but the size of the offsets have been exaggerated. The direction of rotation of plunger 302 is shown by arrow 205.

Figure 11A:
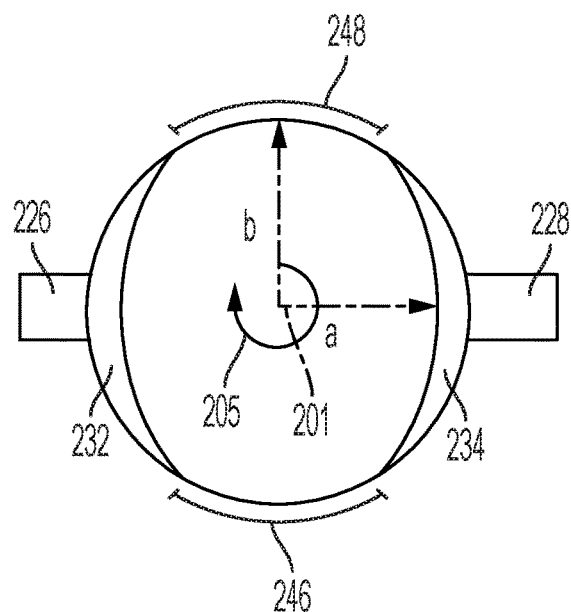
FIGS. 11A, 11B, 11C, and 11D provide illustrative views of inward offsets within the pump housing, according to some embodiments.
Figure 11B:
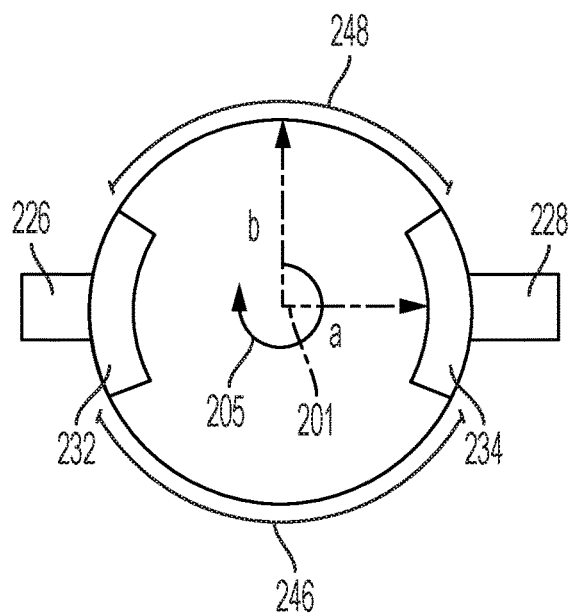
Figure 11C:
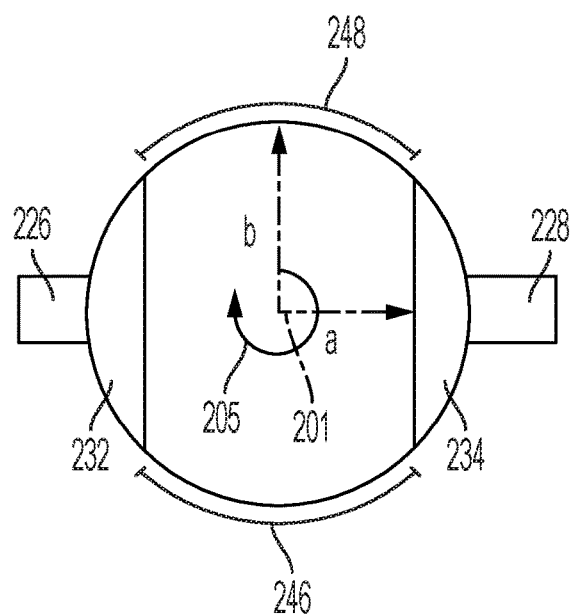
Figure 11D:
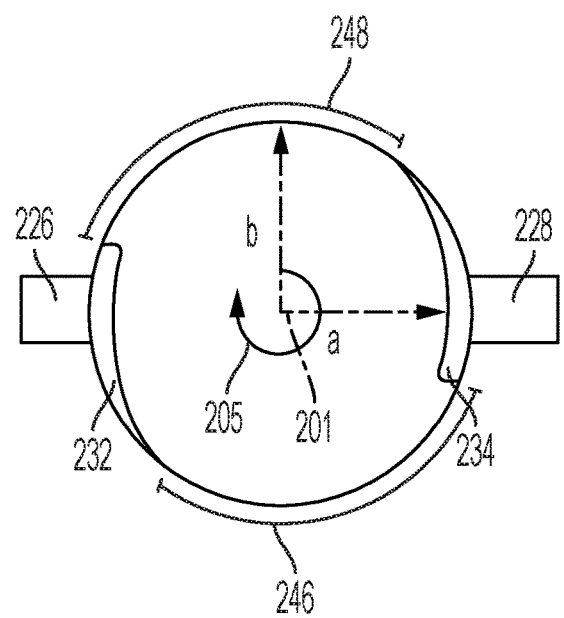

FIG. 11A shows an embodiment in which inwardly offset segments 232, 234 take the form of curved offsets in which both the leading and trailing edge of each offset tapers smoothly as it transitions to the neighboring section of the interior wall of cavity 230. FIG. 11B shows an embodiment in which inwardly offset segments 232, 234 take the form of curved offsets that have an abrupt radial step at both the leading and trailing edge of each offset. FIG. 11C shows an embodiment in which inwardly offset segments 232, 234 take the form of linear offsets. And FIG. 11D shows an embodiment in which the leading edge of each inwardly offset segment tapers smoothly, but the trailing edge of each inwardly offset segment takes the form of an abrupt radial step. In each embodiment, the cross-section of housing 202 is non-circular such that a first constant or varying radial distance "a" from longitudinal axis 201 to one or both of inwardly offset segments 232, 234 is less than a second constant or varying radial distance "b" from longitudinal axis 201 to a portion of the side wall 224 spaced apart from the inlet and outlet ports (e.g., second segments 246, 248).

Inwardly offset segments with abrupt radial steps may be easier to manufacture and assemble. However abrupt radial steps may be undesirable because the elastomeric plunger may experience a sudden increase in required force to overcome the step as it rotates. The step may cause the plunger surface to roll, curl over, wrinkle, or be cut to the point of generating particulate, all of which are undesirable outcomes for device integrity and sealing. Inwardly offset segments with tapered leading edges (e.g., as shown in FIGS. 11A and 11D) permits gradual compression of the elastomer on the plunger 302, which may mitigate at least some of the negative effects listed above. Tapering on trailing edges may be less critical as they are less likely to cause the plunger surface to roll, curl over, wrinkle, or be cut.

Figure 12:
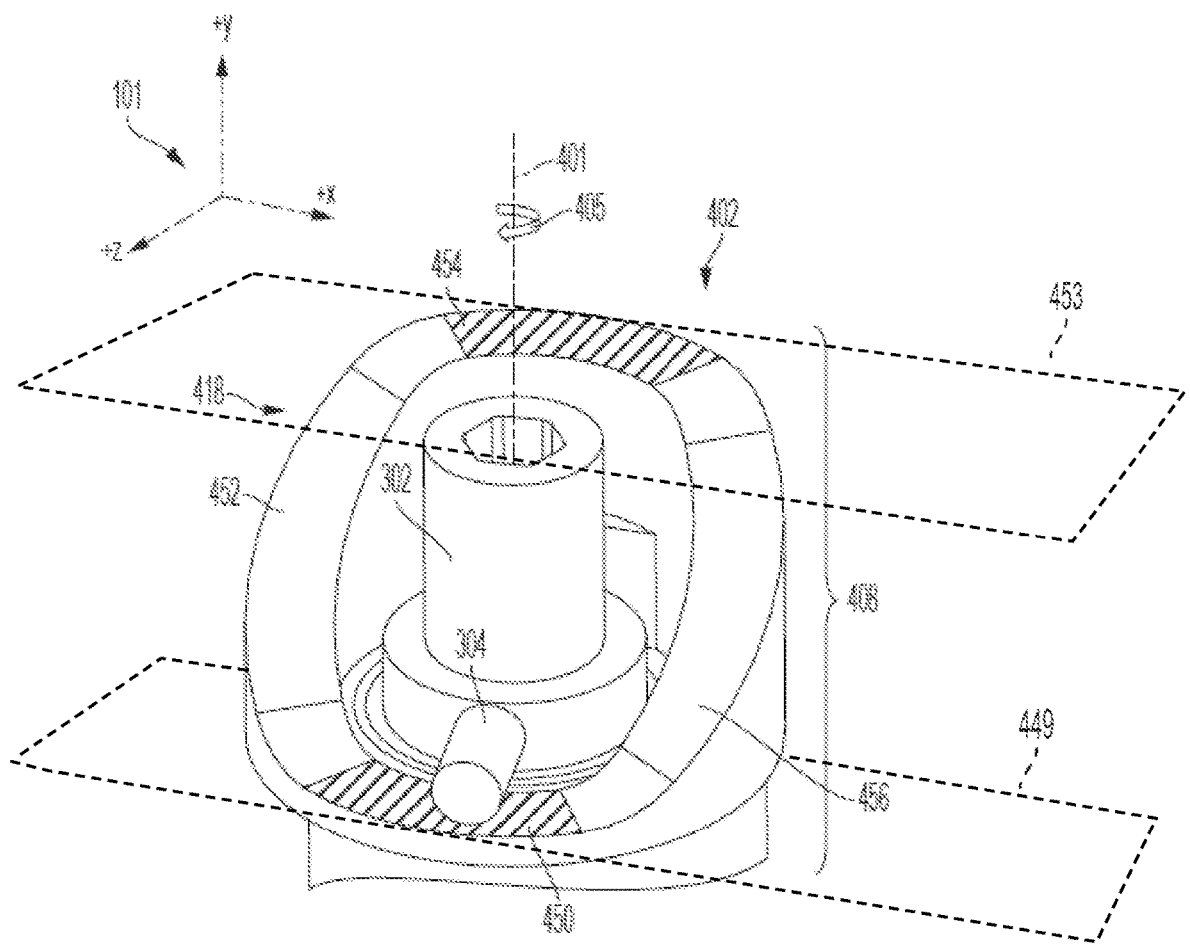
FIG. 12 provides a perspective view of an alternate pump housing component, according to some embodiments.
Figure 13:
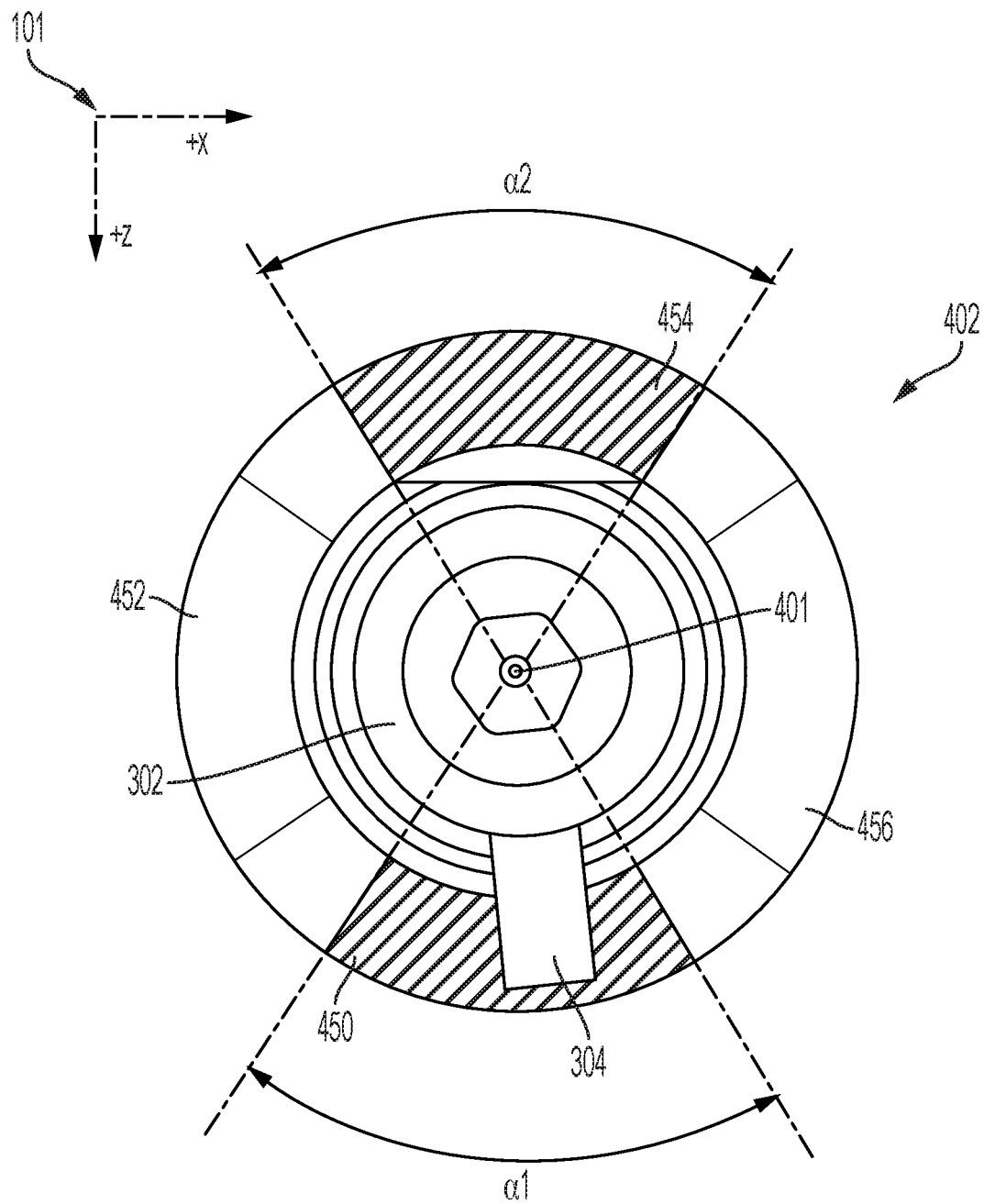
FIG. 13 provides a top-down view of the alternate pump housing component, according to some embodiments.
Figure 14:
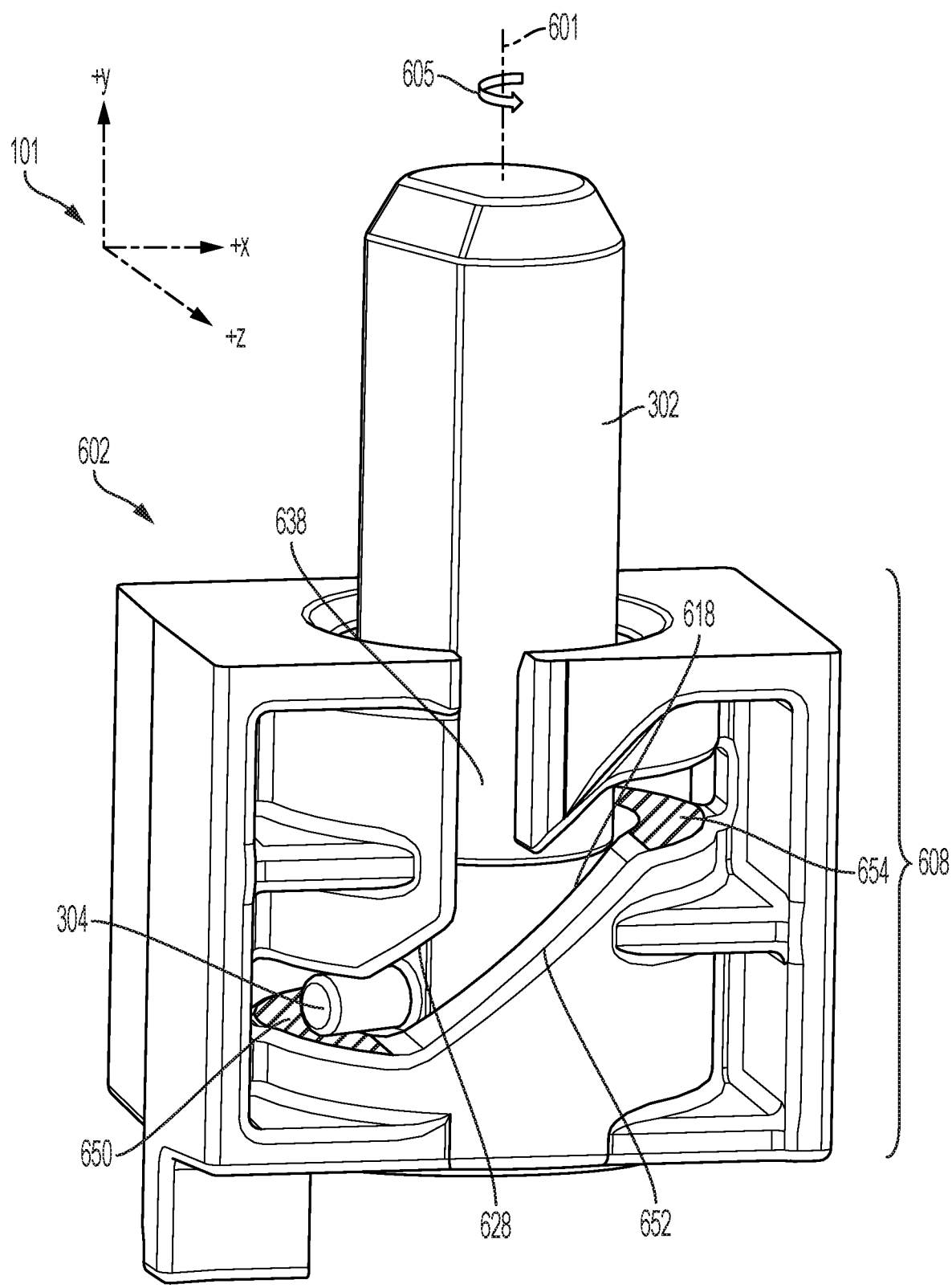
FIGS. 14, 15, 16 and 17 provide perspective views of another alternate pump housing component, according to some embodiments.
Figure 15:
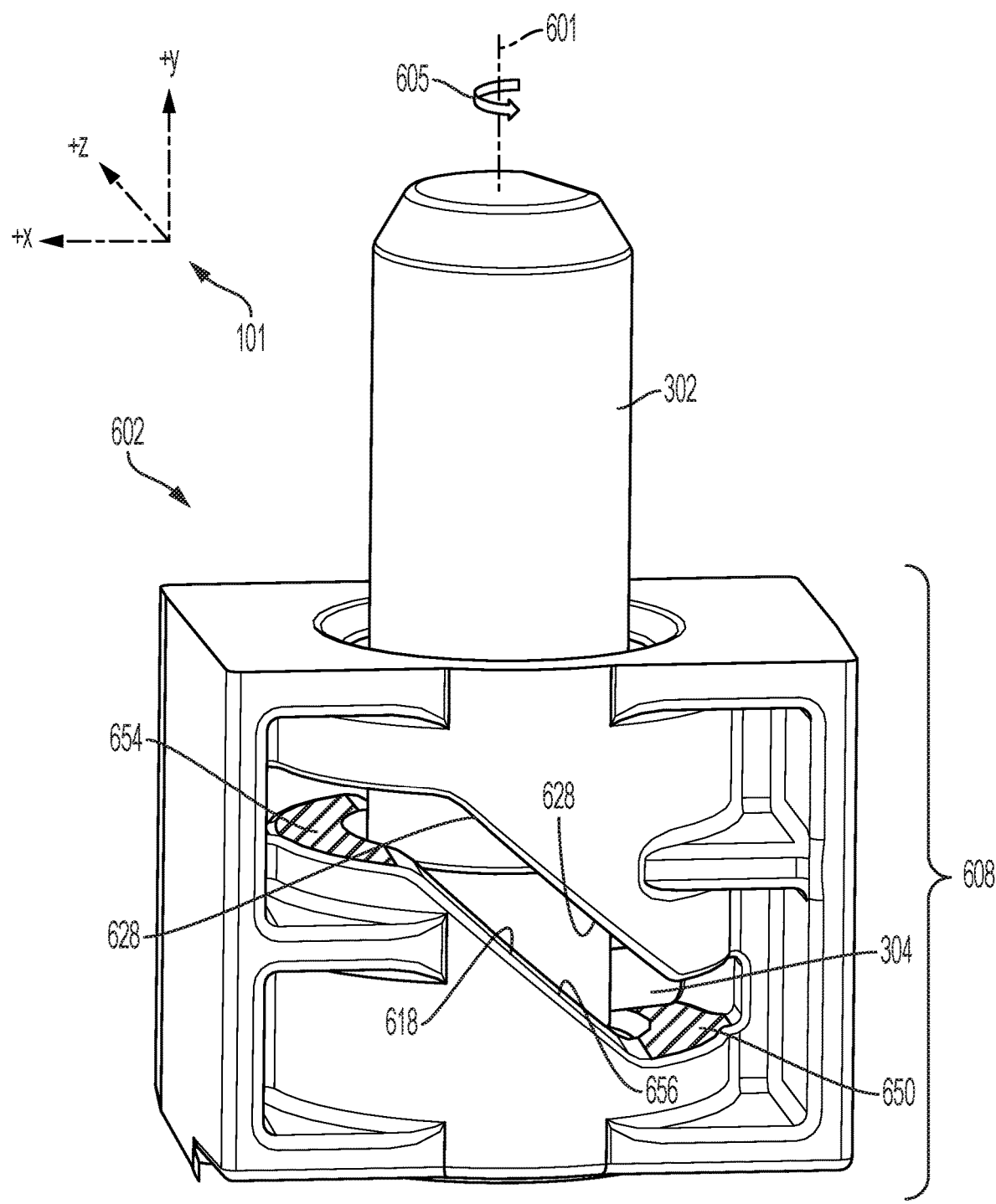
Figure 16:
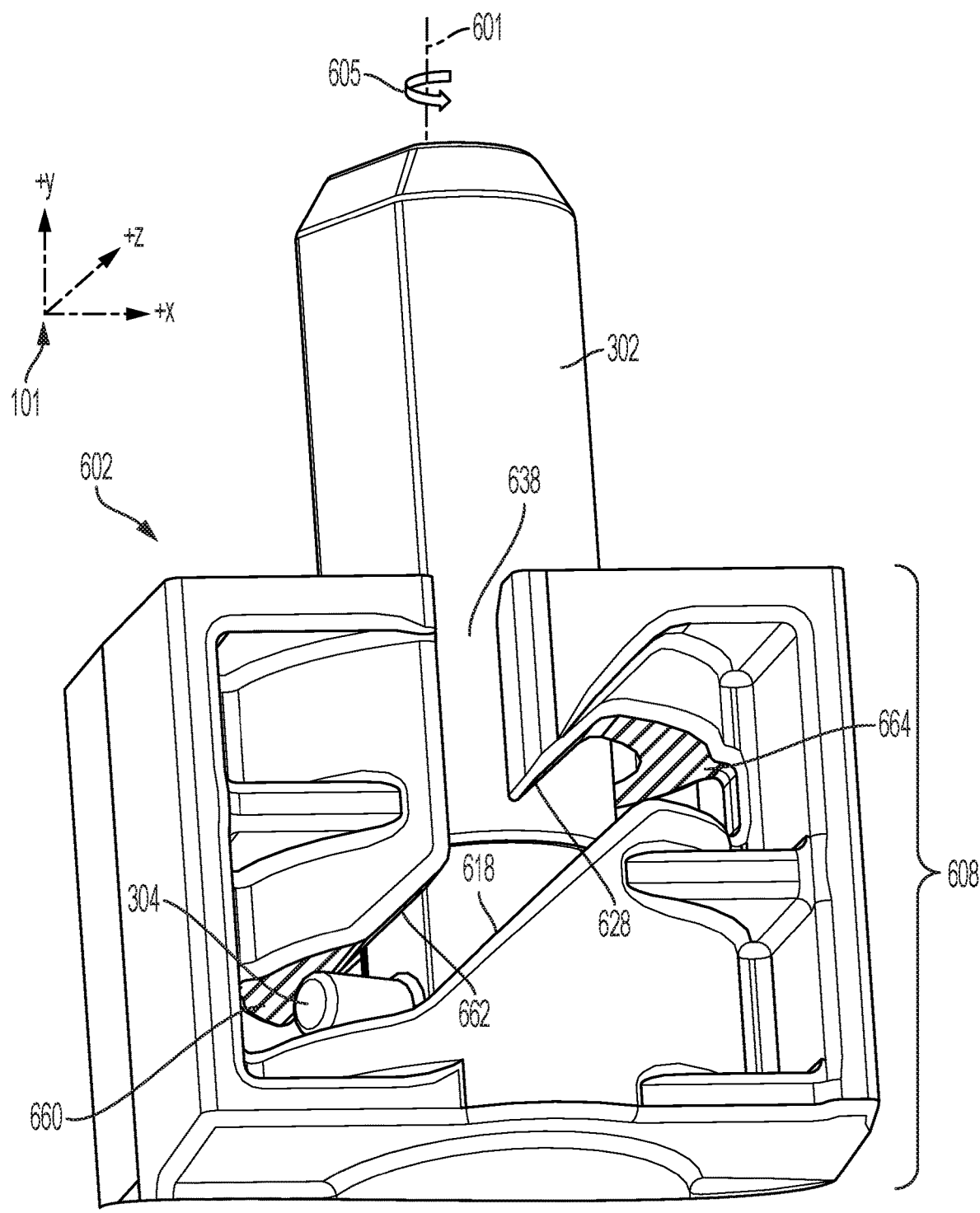
Figure 17:
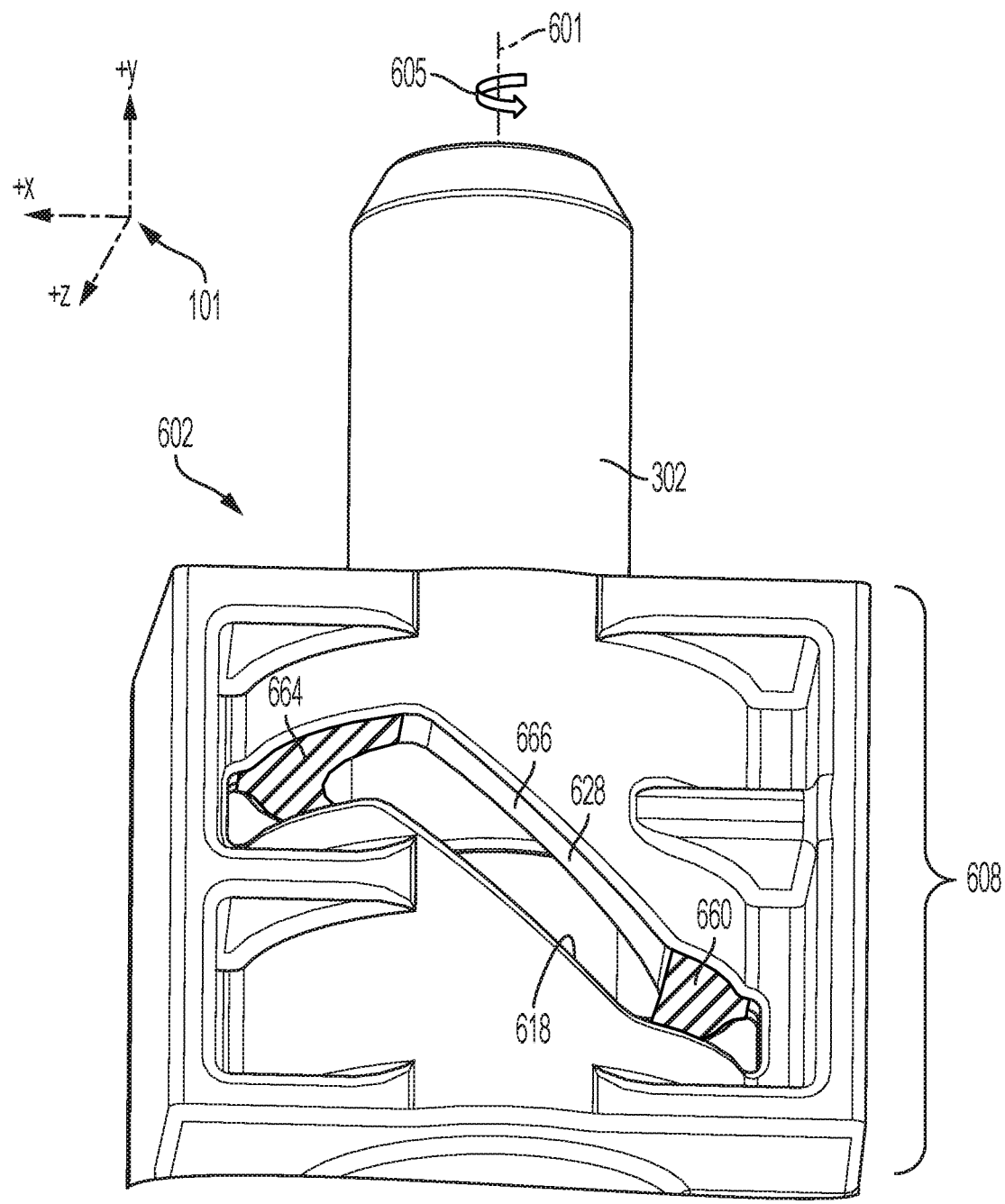

FIGS. 12 and 13 depict an alternate pump housing 402, according to some embodiments. Pump housing 402 is similar to housing 202 in many respects, and elements not specifically mentioned herein may be configured similarly between the two housings. Just as with housing 202, pump housing 402 receives a plunger 302 having a plunger pin 304 that protrudes radially outward. Plunger 302 rotates about longitudinal axis 401 in the direction of arrow 405 (e.g., in a clockwise direction). Proximal section 408 of housing 402 also comprises an angled pin track 418 analogous to angled pin track 218 of housing 202. However, track 418 may be shaped differently than track 218. In some embodiments, track 218 of housing 202 may be shaped as one smoothly continuous curve (e.g., an ellipse), such that plunger 302 constantly changes elevation (i.e., constantly translates longitudinally in the proximal or distal direction) as plunger pin 304 rotates about pin track 218. In contrast, track 418 comprises a distal end section 450 and a proximal end section 454 (indicated using hash marks) that are substantially flat. Distal end section 450 extends along a plane 449 (illustrated using dashed lines) that is perpendicular to longitudinal axis 401; similarly, proximal end section 454 extends along a plane 453 (illustrated using dashed lines) that is perpendicular to longitudinal axis 401 and that is proximal to plane 449. As a result, when plunger pin 304 traverses distal end section 450 and proximal end section 454 as it rotates about axis 401, plunger pin 304 does not change elevation, i.e., does not translate longitudinally, either in the proximal or distal direction. Instead, plunger pin 304 only changes elevation when it engages against upwardly-sloping portion 452 or downwardly-sloping portion 456 of pin track 418.

FIG. 13 provides a top-down view of housing 402 and plunger 302 when viewed from the positive y direction. As shown, the flat distal end section 450 allows plunger 302 to rotate about an angle $\alpha 1$ around axis 401 without changing elevation. Similarly, the flat proximal end section 454 allows plunger 302 to rotate about an angle $\alpha 2$ around axis 401 without changing elevation. In some embodiments, angles $\alpha 1$ and $\alpha 2$ are equal to each other; in other embodiments, angles $\alpha 1$ and $\alpha 2$ are different from each other. In some embodiments, both angles $\alpha 1$ and $\alpha 2$ are less than or equal to 40°. In some embodiments, both angles $\alpha 1$ and $\alpha 2$ are less than or equal to 30°. In some embodiments, both angles $\alpha 1$ and $\alpha 2$ are less than or equal to 20°. In yet other embodiments, both angles $\alpha 1$ and $\alpha 2$ are less than or equal to 10°.

The flat sections 450, 454 allow the pump subsystem to achieve greater consistency in volumes of liquid pumped per pump cycle. As previously-described, the pin 304 should ideally be positioned exactly perpendicular to the orientation of cutout 310. During manufacturing, however, individual pump subsystems may exhibit slight variations in the orientation of pin 304 relative to cutout 310, such that the two components may not be oriented exactly perpendicular to each other. These slight differences in orientation may introduce variations in volume of liquid pumped per stroke cycle between individual pump subsystems. This is because a variation in orientation between pin 304 relative to cutout 310 may cause working chamber 602 to be opened and/or closed to fluid communication with ports 226, 228 at a different point in the pump cycle.

As an illustrative example: assume pin track 218 is shaped as one continuous curve (as may be the case with pin track 218), and that pin 304 of plunger 302 is positioned exactly perpendicular to cutout 310. In this scenario, working chamber 602 may be opened to inlet port 226 when plunger 302 has translated 10% of the way from its furthest distal position to its furthest proximal position; and closed to inlet port 226 when plunger 302 has translated 90% of the way to its furthest proximal position. Similarly, working chamber 602 may be opened to outlet port 228 when plunger 302 has translated 10% of the way from its furthest proximal position to its furthest distal position; and closed to outlet port 228 when plunger 302 has translated 90% of the way to its furthest distal position.

The situation described in this illustrative example means that the pump only pumps fluid when the plunger 302 is between 10% and 90% translated, meaning that 20% of the stroke cycle is wasted. Furthermore, the fact that working chamber 602 is closed to outlet port 228 when plunger 302 has only translated 90% of the way to its furthest distal position leads to greater waste of residual drug fluid compared to situations where fluid communication with outlet port 228 is maintained until plunger 302 has translated 100% of the way to its furthest distal position. This is because any residual drug remaining in working chamber 602 when outlet port 228 is closed as plunger 302 translates from its furthest proximal position to its furthest distal position is generally not pumped, but is instead retained by the pump.

Also, minor variations in manufacturing may cause some pump subsystems to have a pin 304 that is not positioned exactly perpendicular to cutout 310. For example, pin 304 may vary between ±5° of perpendicular. In this case, working chamber 602 may be opened to inlet port 226 when plunger 302 has translated anywhere from 0-25% of the way from its furthest proximal position; and closed to inlet port 226 when plunger 302 has translated anywhere from 75-100% of the way to its furthest proximal position. Similarly, working chamber 602 may be opened to outlet port 228 when plunger 302 has translated anywhere from 0-25% of the way from its furthest proximal position to its furthest distal position; and closed to outlet port 228 when plunger 302 has translated anywhere from 75-100% of the way to its furthest distal position. These ranges are illustrative example ranges only.

These variations in the longitudinal position of plunger 302 when fluid communication to ports 226, 228 is opened or closed can lead to variations in pump stroke length. These variations in the pump stroke length in turn can lead to variations in the amount of fluid pumped with each pump cycle when comparing different pump subsystems. Such variations in volume are undesirable in certain applications, such as in delivery of drug fluids where accuracy of dose is important.

The flat sections 450, 454 of housing 402 mitigate these variations in volume. Specifically, the flat section 450 helps ensure that fluid communication between working chamber 602 and inlet port 226 is opened before plunger 302 begins translating upwards from its furthest distal position to its furthest proximal position. As plunger 302 continues its rotation, flat section 454 helps ensure that plunger 302 completes its upward translation to its furthest proximal position before fluid communication between working chamber 602 and inlet port 226 is closed. Further on in the pump cycle, flat section 454 also helps ensure that fluid communication between working chamber 602 and outlet port 228 is opened before plunger 302 begins its downward translation from its furthest proximal position to its furthest distal position. Finally, flat section 450 helps ensure that plunger 302 completes its downward translation from its furthest proximal position to its furthest distal position before fluid communication between working chamber 602 and outlet port 228 is closed. Flat sections 450, 454 help ensure the above timing of events even if pin 304 of plunger 302 is not positioned exactly perpendicular to cutout 310, but is instead slightly offset by a few degrees from perpendicular. In this way, flat sections 450, 454 help ensure a more consistent volume of fluid pumped when comparing different pump subsystems.

Although FIGS. 12-13 show that track 418 has two flat sections 450, 454, some embodiments of housing 408 may comprise only one flat section. For example, housing 408 may comprise only flat distal end section 450, and not flat proximal end section 454, or vice versa.

FIGS. 14, 15, 16, and 17 depict another alternate pump housing 602, according to some embodiments. Pump housing 602 is similar to housing 202 and housing 402 in many respects, and elements not specifically mentioned herein may be configured similarly between these housings. Pump housing 602 comprises a proximal section 608 that is similar to proximal section 408 of housing 402: pump housing 602 receives a plunger 302 having a plunger pin 304 that protrudes radially outward. Plunger 302 rotates about longitudinal axis 601 in the direction of arrow 605, i.e., in the counter-clockwise direction as shown in the figures. However, whereas housing 402 comprises a single angled pin track 418, housing 602 comprises two pin tracks: an upward-facing angled pin track 618 analogous to pin track 418, and a downward-facing angled pin track 628. Similar to pin tracks 218 and 418, upward-facing angled pin track 618 is configured to contact a distal side of plunger pin 304. Downward-facing angled pin track 628 is configured to contact a proximal side of plunger pin 304.

Upward-facing angled pin track 618 comprises a flat distal end section 650 (analogous to flat distal end section 450) and a flat proximal end section 654 (analogous to flat proximal end section 454). The two flat sections 650, 654 are connected by an upwardly-sloping section 652 and a downwardly-sloping section 656. Downward-facing angled pin track 628 comprises a flat distal end section 660 and a flat proximal end section 664 (see FIGS. 16 and 17). The two flat sections 660, 664 are connected by an upwardly-sloping section 662 and a downwardly-sloping section 666.

During rotation of plunger 302 within housing 602, the upward-facing track 618 and the downward-facing track 628 cooperate to ensure plunger 302 translates axially upward and downward along longitudinal axis 601. In some embodiments, the use of these two tracks allow plunger 302 to achieve the correct upward and downward longitudinal translation without the aid of return spring 124. This allows the pump subsystem to function with just a rotary input, and simplifies construction and assembly of the pump subsystem.

After pin 304 completes its traversal of flat distal end section 650, pin 304 encounters the upwardly-sloping portion 652 of upward-facing track 618. The upwardly-sloping portion 652 causes pin 304 (and therefore plunger 302) to translate upwards, i.e., in the proximal direction, as pin 304 rotates. This upward translation continues until pin 304 reaches flat proximal end section 654, at which point pin 304 stops its upward translation. When pin 304 completes its traversal of flat proximal end section 654, it encounters the downwardly-sloping portion 666 of downward-facing track 628. The downwardly-sloping portion 666 causes pin 304 (and therefore plunger 302) to translate downwards, i.e., in the distal direction, as pin 304 rotates. This downward translation continues until pin 304 again reaches distal end section 654, at which point pin 304 stops its downward translation.

Additionally, housing 602 comprises a vertical insertion slot 638 formed in the side wall of the housing. Insertion slot 638 is positioned to interrupt upward-sloping section 662 of downward-facing track 628. The insertion slot 638 allows plunger pin 304 to be slotted into place within housing 602 during assembly. In operation, since the pin 304 consistently rides the upwardly-sloping section 652 of upward-facing track 618 at this point in the pump cycle, the risk of disassembly through the open slot 638 during normal operation is mitigated. In some embodiments, however, vertical slot 638 may be closed or blocked using a movable door or member that prevents pin 304 from exiting therethrough after assembly. In some embodiments, pin 304 may be collapsible or may be assembled into plunger 302 after plunger 302 is assembled into housing 602; in such embodiments, there may not be any need for vertical slot 638 at all, and upwardly-sloping section 662 may be a continuous surface mirroring upwardly-sloping portion 652.

Although FIGS. 14-17 depict an upward-facing track 618 and a downward-facing track 628 having flat end sections, some embodiments may comprise both an upward-facing track and a downward-facing track that have no flat end sections, or that each have only one flat end section.

The terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A rotary sub-assembly for pumping of drug fluid in a drug-delivery device, said sub-assembly comprising:
   a hollow body comprising a housing side wall defining a cavity extending about a longitudinal axis between a closed distal end and an open proximal end, the housing side wall including at least two ports passing therethrough and in fluid communication with the cavity, wherein at least a working portion of the cavity has a non-circular cross-section extending along a plane perpendicular to the longitudinal axis, the working portion being defined by first inwardly-offset segments of the housing side wall interconnected by second segments of the housing side wall, the first inwardly-offset segments spaced from the longitudinal axis by a constant or varying first radial distance, and the second segments spaced from the longitudinal axis by a constant or varying second radial distance that is greater than the first radial distance, wherein said first inwardly-offset segments of the housing side wall are disposed along regions of the side wall surrounding the two ports, and said second segments of the housing side wall are spaced apart from the two ports; and
   a plunger housed in the cavity defining a working chamber between the plunger and the housing side wall, wherein:
      the plunger is configured to rotate relative to the body in order to put the working chamber into sequential fluid-flow communication with at least one port of the two ports, then no port, then at least the other of said two ports,
      the plunger is further configured to move in longitudinal translation relative to the body and thereby cause a volume of said working chamber to vary in order to successively take in a drug fluid from one of the two ports and then to discharge the fluid from the other of the two ports, and the plunger is sized and shaped such that when the working chamber is in fluid-flow communication with one of the two ports, a side wall of the plunger establishes a liquid-tight seal against the first inwardly-offset segment of the housing side wall surrounding the other port of the two ports, but does not establish a liquid-tight seal with the second segments of the housing side wall.

2. The rotary sub-assembly of claim 1, wherein the plunger further comprises a plunger pin extending radially outward from the plunger.

3. The rotary sub-assembly of claim 2, wherein the body further comprises a first pumping track configured to slidably contact a distal side of the plunger pin as the plunger rotates relative to the body, wherein the pumping track comprises at least one flat section extending along a plane that is perpendicular to the longitudinal axis.

4. The rotary sub-assembly of claim 3, wherein the pumping track comprises both a distal flat section extending along a plane that is perpendicular to the longitudinal axis and a proximal flat section extending along a different plane that is perpendicular to the longitudinal axis.

5. The rotary sub-assembly of claim 2, wherein the body further comprises a first pumping track configured to slidably contact a distal side of the plunger pin, and a second pumping track configured to slidably contact a proximal side of the plunger pin.

6. The rotary sub-assembly of claim 5, wherein the first pumping track and the second pumping track each comprise at least one flat section extending along a plane that is perpendicular to the longitudinal axis.

7. The rotary sub-assembly of claim 1, wherein:

a portion of the cavity has a circular cross-section along a plane perpendicular to the longitudinal axis, the plunger further comprises a proximal annular sealing rib and a distal annular sealing rib longitudinally spaced from one another, wherein both annular sealing ribs contact a portion of the housing side wall defining the portion of the cavity having the circular cross-section so as to establish a liquid-tight seal that seals the working chamber from the open proximal end of the cavity.

8. The rotary sub-assembly of claim 7, wherein:

the plunger is configured to move in longitudinal translation relative to the body between a proximal plunger position and a distal plunger position; and both annular sealing ribs on the plunger are located proximal to the two ports opening out into the cavity when the plunger is in its distal plunger position.

9. The rotary sub-assembly of claim 8, wherein a longitudinal distance between the two annular sealing ribs is no less than a longitudinal distance between the proximal plunger position and the distal plunger position.

10. The rotary sub-assembly of claim 1, wherein each of the first inwardly-offset segments of the housing side wall comprises a first edge that transitions smoothly to a first neighboring edge of said second segments of the housing side wall, and a second edge that transitions abruptly to a second neighboring edge of said second segments of the housing side wall.

11. A drug-delivery device comprising:

a drug reservoir storing a drug fluid; and the rotary sub-assembly of claim 1 for pumping the drug fluid from the drug reservoir for delivery to a patient.

* * * * *